US009657077B2

(12) United States Patent
Li et al.

(10) Patent No.: US 9,657,077 B2
(45) Date of Patent: May 23, 2017

(54) CARCINOMA HOMING PEPTIDE (CHP), ITS ANALOGS, AND METHODS OF USING

(75) Inventors: Shulin Li, Houston, TX (US); Jeffry Cutrera, Houston, TX (US); Xueqing Xia, Houston, TX (US)

(73) Assignees: BOARD OF SUPERVISORS OF LOUISIANA STATE; UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 1030 days.

(21) Appl. No.: 13/370,011

(22) Filed: Feb. 9, 2012

(65) Prior Publication Data

US 2012/0208770 A1 Aug. 16, 2012

Related U.S. Application Data

(60) Provisional application No. 61/441,914, filed on Feb. 11, 2011.

(51) Int. Cl.

| | |
|---|---|
| *A61K 6/00* | (2006.01) |
| *A61K 31/70* | (2006.01) |
| *A61K 31/7088* | (2006.01) |
| *A61K 38/00* | (2006.01) |
| *A61K 38/16* | (2006.01) |
| *A61K 38/17* | (2006.01) |
| *A61K 38/19* | (2006.01) |
| *A61K 38/20* | (2006.01) |
| *A61K 39/00* | (2006.01) |
| *A61K 39/395* | (2006.01) |
| *C07K 14/54* | (2006.01) |
| *C07K 7/06* | (2006.01) |
| *G01N 33/574* | (2006.01) |

(52) U.S. Cl.
CPC ...... *C07K 14/5434* (2013.01); *A61K 31/7088* (2013.01); *A61K 38/208* (2013.01); *C07K 7/06* (2013.01); *G01N 33/57415* (2013.01); *G01N 33/57419* (2013.01); *G01N 33/57423* (2013.01); *G01N 33/57492* (2013.01); *C07K 2319/33* (2013.01); *G01N 2800/52* (2013.01)

(58) Field of Classification Search
None
See application file for complete search history.

(56) References Cited

U.S. PATENT DOCUMENTS

2009/0215879 A1* 8/2009 Diprimio et al. ........... 514/44 R

FOREIGN PATENT DOCUMENTS

WO WO 2008/152508 A2 * 12/2008

OTHER PUBLICATIONS

Bhattacharya, R. et al., "Recruitment of vimentin to the cell surface by beta3 integrin and plectin mediates adhesion strength," J Cell Sci , vol. 122, pp. 1390-1400 (2009).
Colombo, G. et al., "Structure-activity relationships of linear and cyclic peptides containing the NGR tumor-homing motif," J Biol Chem, vol. 277, pp. 47891-47897 (2002).
Corti, A. et al., "The neovasculature homing motif NGR: more than meets the eye," Blood, vol. 112, pp. 2628-2635 (2008).
Craig, R. et al., "Administering plasmid DNA encoding tumor vessel-anchored IFN-alpha for localizing gene product within or into tumors," Mol Ther, vol. 16, pp. 901-906 (2008).
Creighton, C.J. et al., "Residual breast cancers after conventional therapy display mesenchymal as well as tumor-initiating features," Proc Natl Acad Sci U S A, vol. 106, pp. 13820-13825 (2009).
Cutrera, J. et al., "Discovery of a Linear Peptide for Improving Tumor Targeting of Gene Products and Treatment of Distal Tumors by IL-12 Gene Therapy," www.moleculartherapy.org, vol. 19, No. 8, pp. 1468-1477 (2011).
Cutrera, J. et al., "Enhancement of reporter gene detection sensitivity by insertion of specific mini-peptide-coding sequences," Cancer Gene Ther, vol. 17, pp. 131-140 (2010).
Dandachi, N. et al., "Co-expression of tenascin-C and vimentin in human breast cancer cells indicates phenotypic transdifferentiation during tumour progression: correlation with histopathological parameters, hormone receptors, and oncoproteins," J Pathol, vol. 193, pp. 181-189 (2001).
Del Vecchio, M. et al., "Interleukin-12: biological properties and clinical application," Clin Cancer Res, vol. 13, pp. 4677-4685 (2007).
Dela Cruz, J.S. et al., "Recombinant anti-human HER2/neu IgG3-(GM-CSF) fusion protein retains antigen specificity and cytokine function and demonstrates antitumor activity," J Immunol, vol. 165, pp. 5112-5121 (2000).
Dickerson, E.B. et al., "Enhancement of the Antiangiogenic Activity of Interleukin-12 by Peptide Targeted Delivery of the Cytokine to $\alpha_v\beta_3$ Integrin," Mol Cancer Res, vol. 2, pp. 663-673 (2004).
Gafner, S. et al., "Alkaloids from Eschscholzia californica and their capacity to inhibit binding of [3H]8-Hydroxy-2-(di-N-propylamino)tetralin to 5-HT1A receptors in Vitro," J Nat Prod, vol. 69, pp. 432-435 (2006).
Gafner, V. et al., "An engineered antibody-interleukin-12 fusion protein with enhanced tumor vascular targeting properties," Int J Cancer, vol. 119, pp. 2205-2212 (2006).
Gao, J.Q. et al., "Effective tumor targeted gene transfer using PEGylated adenovirus vector via systemic administration," J Control Release, vol. 122, pp. 102-110 (2007).

(Continued)

*Primary Examiner* — Alana Harris Dent
(74) *Attorney, Agent, or Firm* — Venable LLP; Keith G. Haddaway; Miguel A. Lopez

(57) ABSTRACT

A mini-peptide and its analogs have been found to target gene products to tumors. The peptide, named Carcinoma Homing Peptide (CHP), increased the tumor accumulation of the reporter gene products in five independent tumor models, including one human xenogeneic model. A CHP-IL-12 fusion gene was also developed using CHP and the p40 subunit of IL-12. The product from CHP-IL-12 fusion gene therapy increased accumulation of IL-12 in the tumor environment. In three tumor models, CHP-IL-12 gene therapy inhibited distal tumor growth. In a spontaneous lung metastasis model, inhibition of metastatic tumor growth was improved compared to wild-type IL-12 gene therapy, and in a squamous cell carcinoma model, toxic liver lesions were reduced. The receptor for CHP was identified as vimentin. CHP can be used to improve the efficacy and safety of targeted cancer treatments.

12 Claims, 16 Drawing Sheets

(56) References Cited

OTHER PUBLICATIONS

Garanger, E. et al., "New multifunctional molecular conjugate vector for targeting, imaging, and therapy of tumors," Mol Ther, vol. 12, pp. 1168-1175 (2005).

Gilles, C. et al., "Vimentin contributes to human mammary epithelial cell migration," J Cell Sci, vol. 112 ( Pt 24), pp. 4615-4625 (1999).

Halin, C. et al., "Enhancement of the antitumor activity of interleukin-12 by targeted delivery to neovasculature," Nat Biotechnol, vol. 20, pp. 264-269 (2002).

Huet, D. et al., "SC5 mAb represents a unique tool for the detection of extracellular vimentin as a specific marker of Sezary cells," J Immunol, vol. 176, pp. 652-659 (2006).

Kobayashi, M. et al., "Identification and purification of natural killer cell stimulatory factor (NKSF), a cytokine with multiple biologic effects on human lymphocytes," J Exp Med, vol. 170, pp. 827-845 (1989).

Li, S. et al., "Administration route- and immune cell activation-dependent tumor eradication by IL-12 electrotransfer," Mol Ther, vol. 12, pp. 942-949 (2005).

Maeda, H. et al., "Vascular permeability enhancement in solid tumor: various factors, mechanisms involved and its implications," Int Immunopharmacol 3, pp. 319-328 (2003).

Matos, J.M. et al., "A pilot study of proteomic profiles of human hepatocellular carcinoma in the United States," J Surg Res, vol. 155, pp. 237-243 (2009).

Moisan, E. et al., "Cell surface expression of intermediate filament proteins vimentin and lamin B1 in human neutrophil spontaneous apoptosis," J Leukoc Biol, vol. 79, pp. 489-498 (2006).

Ngan, C.Y. et al., "Quantitative evaluation of vimentin expression in tumour stroma of colorectal cancer," Br J Cancer, vol. 96, pp. 986-992 (2007).

Nieminen, M. et al., "Vimentin function in lymphocyte adhesion and transcellular migration," Nat Cell Biol, vol. 8, pp. 156-162 (2006).

Okada, Y. et al., "Optimization of antitumor efficacy and safety of in vivo cytokine gene therapy using RGD fiber-mutant adenovirus vector for preexisting murine melanoma," Biochim Biophys Acta, vol. 1670, pp. 172-180 (2004).

Sancey, L. et al., "Clustering and internalization of integrin alphavbeta3 with a tetrameric RGD-synthetic peptide," Mol Ther, vol. 17, pp. 837-843 (2009).

Stoff-Khalili, M.A. et al., "Cancer-specific targeting of a conditionally replicative adenovirus using mRNA translational control," Breast Cancer Res Treat, vol. 108, pp. 43-55 (2008).

Temming, K. et al., "RGD-based strategies for selective delivery of therapeutics and imaging agents to the tumour vasculature," Drug Resist Updat, vol. 8, pp. 381-402 (2005).

Thiery, J.P., "Epithelial-mesenchymal transitions in tumour progression," Nat Rev Cancer, vol. 2, pp. 442-454 (2002).

Wang, H. et al., "Integrin-targeted imaging and therapy with RGD4C-TNF fusion protein," Mol Cancer Ther, vol. 7, pp. 1044-1053 (2008).

Wang, Z. et al., "Acquisition of epithelial-mesenchymal transition phenotype of gemcitabine-resistant pancreatic cancer cells is linked with activation of the notch signaling pathway," Cancer Res, vol. 69, pp. 2400-2407 (2009).

Work, L.M. et al., "Vascular Bed-Targeted in Vivo Gene Delivery Using Tropism-Modified Adeno-associated Viruses," Molecular Therapy, vol. 13, pp. 638-693 (2006).

Yamazaki, M. et al., "Effective gene therapy for medullary thyroid carcinoma using recombinant adenovirus inducing tumor-specific expression of interleukin-12," Gene Ther, vol. 9, pp. 64-74 (2002).

Zhu, S. et al., "IL-12 and IL-27 sequential gene therapy via intramuscular electroporation delivery for eliminating distal aggressive tumors," J Immunol, vol. 184, pp. 2348-2354 (2010).

\* cited by examiner

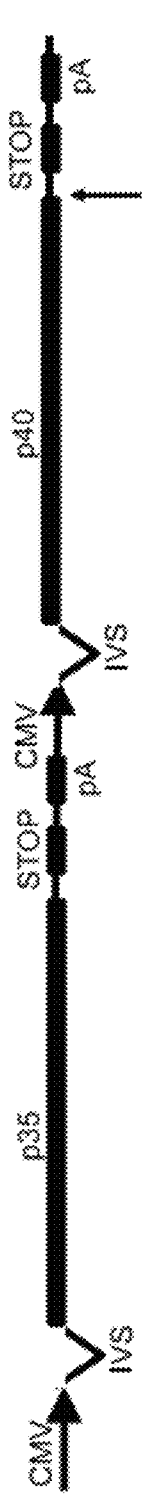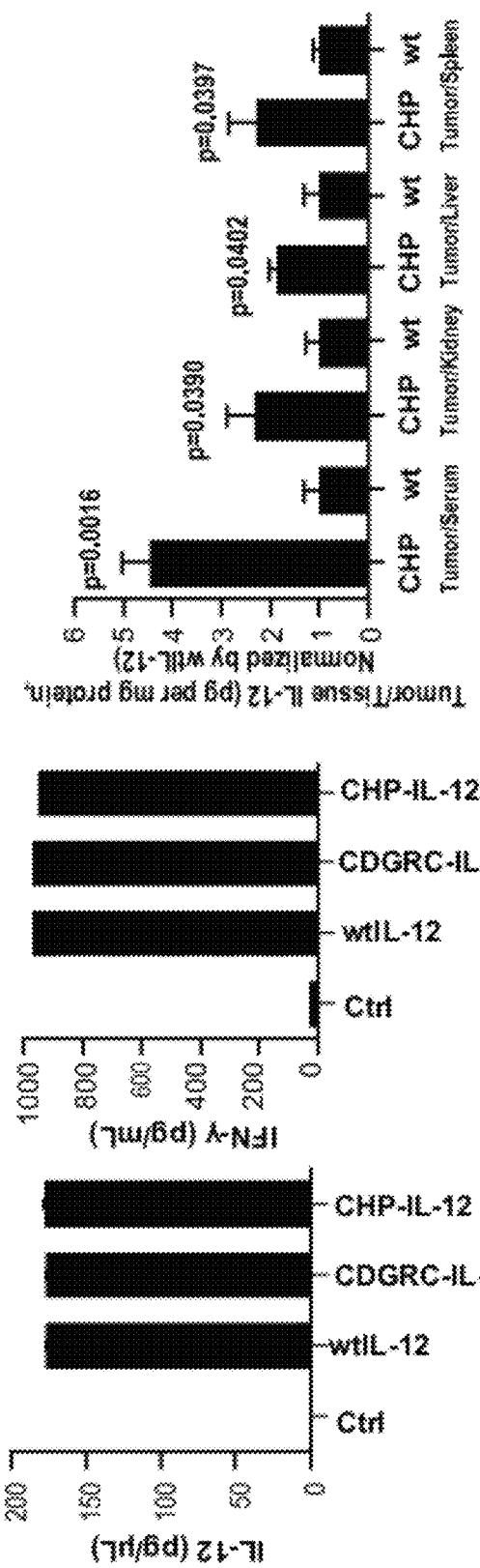

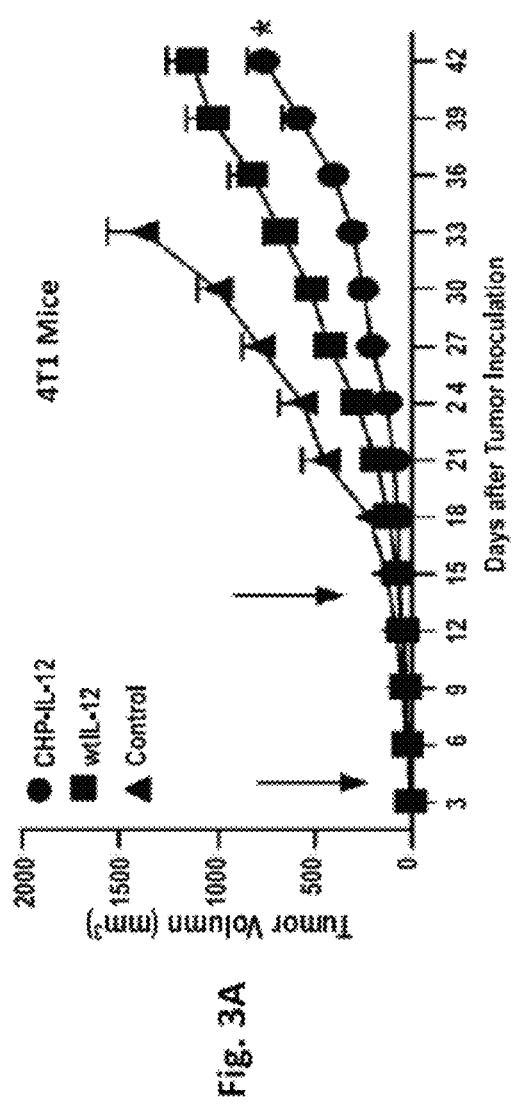
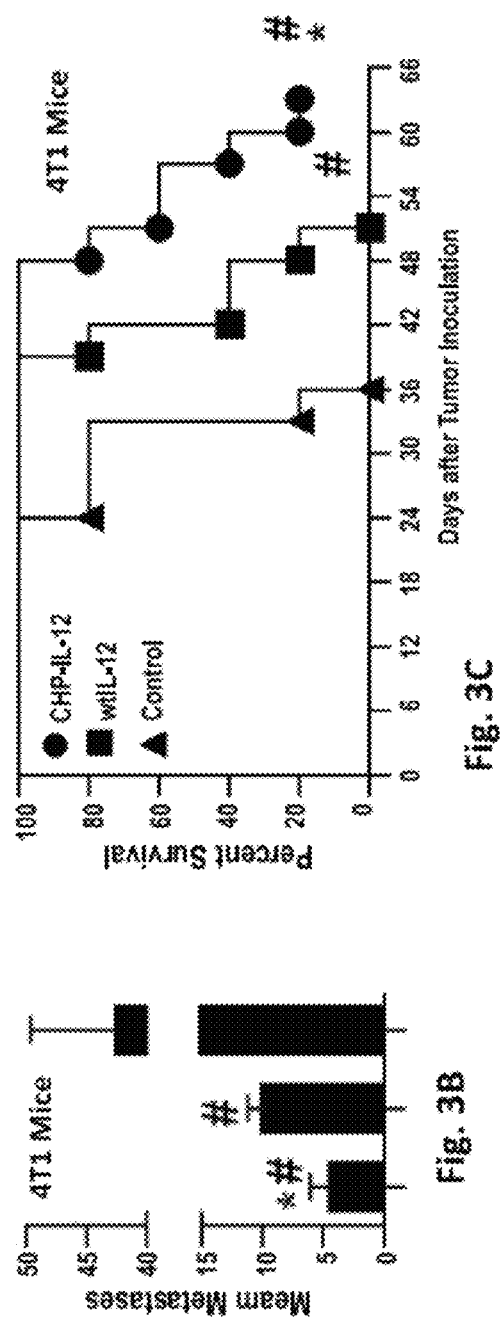
Fig. 3A
Fig. 3B
Fig. 3C

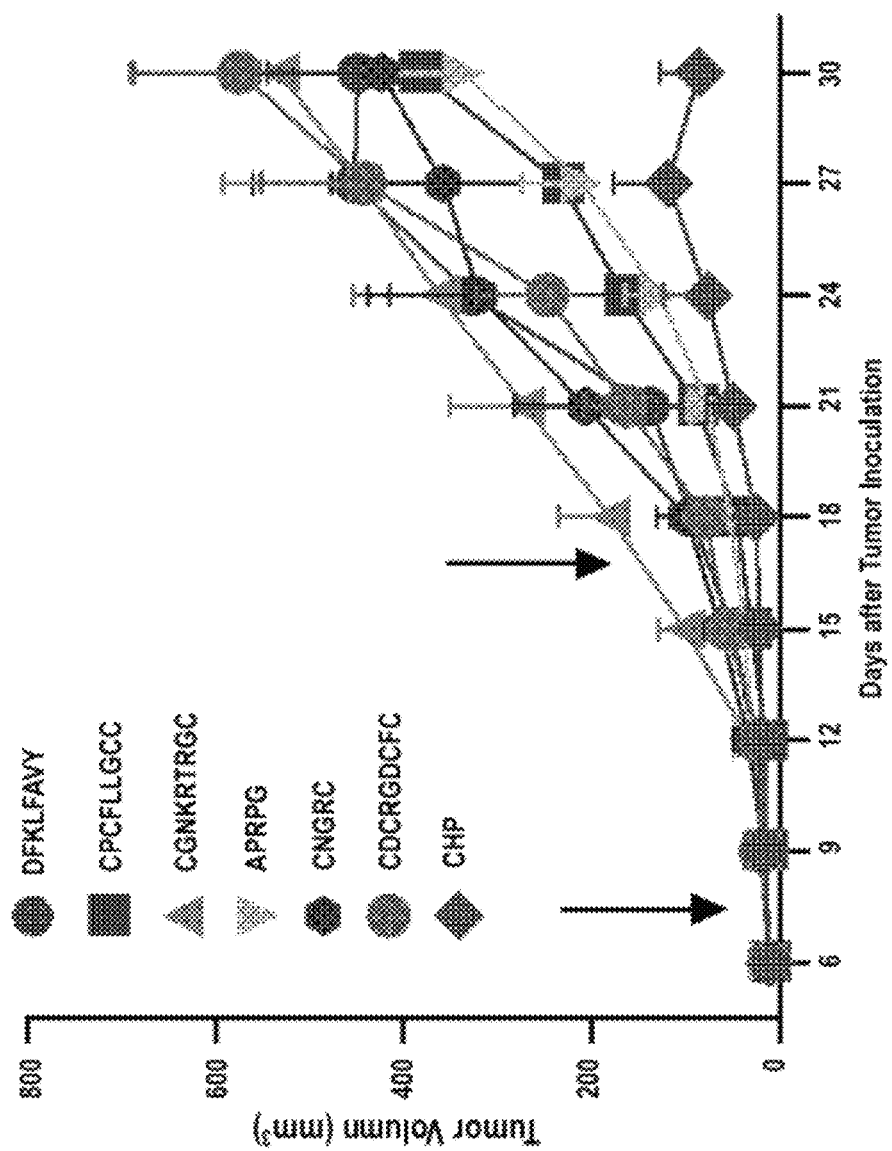

CARCINOMA HOMING PEPTIDE (CHP), ITS ANALOGS, AND METHODS OF USING

The benefit of the Feb. 11, 2011 filing date of the U.S. provisional patent application Ser. No. 61/441,914 is claimed under 35 U.S.C. §119(e).

This invention was made with government support under grant number R01 CA120895 awarded by the National Institutes of Health. The government has certain rights in this invention.

TECHNICAL FIELD

This invention pertains to a carcinoma homing peptide and its analogs, compounds, and methods that target tumors, and methods to use these peptides including targeting, decreasing the size of, inhibiting growth of, and identification of mammalian tumors, such as breast adenocarcinoma, squamous cell carcinoma, and colon carcinoma.

BACKGROUND ART

The cytokine, interleukin 12 (IL-12), discovered by Giorgio Trinchieri in 1989 [1], bridges the innate and adaptive immune responses by inducing interferon-γ (IFN-γ) production primarily from natural killer and T cells. Cancer therapy with IL-12 exploits its natural immune functions to polarize T cells to the $T_h1$ phenotype, boost effector T cells, downregulate angiogenesis, remodel the extracellular matrix, and alter the levels of immune suppressive cytokines [2]. Due to these activities, IL-12 is one of the most promising cytokines for immunomodulatory cancer therapy.

The initial clinical trials with IL-12 resulted in grave toxicities including deaths, which severely downgraded the reputation and potential application of this effective cytokine. In reality, most anticancer drugs or biological modalities are associated with systemic toxicity. It is desirable to decrease this toxicity to effectively and safely treat the extremely high numbers of cancer patients [2].

A popular strategy for sequestering the effects of cytokine therapies in the tumor environment is targeting cellular markers that are upregulated exclusively in the tumor cells or the tumor microenvironment. Indeed, conjugating IL-12 to tumor-specific antibodies, such as L19 [3] and HER2 [4], and tumor vasculature-specific peptides, such as RGD [5] and CNGRC (SEQ ID NO.9) [6], improves the efficacy of treatments; however, the necessarily high frequency of administrations of recombinant cytokines increases the immunogenicity, toxicity, and cost of treatments. A gene therapy approach would reduce these limitations.

Intratumoral IL-12 gene therapy is able to eradicate 40% of tumors in a murine squamous cell carcinoma model (SCCVII) while systemic delivery via intramuscular administration fails to eradicate any tumors [7]; however, direct injection into tumor sites is rarely available noninvasively or post-surgically. Several methods have been developed to target the IL-12 effect to the tumor after systemic delivery. For example, modifying viral vectors with tissue specific gene promoters such as the CALC-I promoter [8], capsid-expressed tumor-specific peptides [9], and polyethylene glycol or other nanoparticles [10, 11] increases tumor specific expression and decreases systemic expression; however, the fenestrated vasculature of the tumor environment allows for the gene products to leak out of the tumor environment leading to systemic toxicities [12]. Therefore, a gene product that can interact with and remain in the tumor environment will increase the level of therapeutic efficacy and decrease systemic toxicity.

Tumor targeting can be achieved via the screening of various libraries to select tumor-targeted peptides, DNA/RNA aptamers, antibodies, etc; however, the only mechanism that can be used for homing gene products from systemically injected genes will be tumor-targeted minipeptides encoding DNA. The small size of these peptides eliminates the concern of immunogenicity, and reduces the effect on the biological function of the gene product, though some minipeptides may boost or inhibit gene function [20]. The tiny peptide encoding DNA sequences can be easily fused with any therapeutic gene. Finally, these peptides can complement existing tumor targeting approaches such as transcriptional targeting [8], translational targeting [21], and targeted delivery [3-6].

Currently, most tumor-targeting strategies are based on extremely specific interactions, and the ability to target the tumor environment is constrained to a single cell type or specific type of tumor. Proteins are conjugated with polyunsaturated fatty acids, monoclonal antibodies, folic acid, peptides, and several other chemicals to increase the tumor-targeted ability of the therapeutic protein. Other tumor targeting peptides can deliver small molecules with only one copy for each small-molecule payload but require multiple copies of the peptide to target larger molecules such as a full length cytokine [24].

DISCLOSURE OF THE INVENTION

We have discovered a new tumor targeting peptide, VNTANST (SEQ ID NO:1), and its analogs. A DNA fragment encoding VNTANST (SEQ ID NO:1) was inserted directly before the stop codon of the p40 subunit of the IL-12 encoding sequence in plasmid DNA. Transfection of this plasmid DNA via intramuscular (i.m.) electroporation (EP) into muscle tissue distal from the tumor site inhibited tumor growth and extended survival in multiple tumor models and two mouse strains and reduced lung metastasis in a spontaneous metastatic model. Due to this broad targeting nature and to simplify the description, the peptide VNTANST (SEQ ID NO:1) was renamed the Carcinoma Homing Peptide (CHP). We discovered that the linear peptide VNTANST (SEQ ID NO:1) increased the tumor accumulation of the reporter gene products in five independent tumor models including one human xenogeneic model. The product from VNTANST-IL-12 fusion gene therapy increased accumulation of IL12 in the tumor environment, and in three tumor models, VNTANST-IL-12 gene therapy inhibited distal tumor growth. In a spontaneous lung metastasis model, inhibition of metastatic tumor growth was improved compared to wild-type (wt) IL-12 gene therapy, and in a squamous cell carcinoma model, toxic liver lesions were reduced. The receptor for VNTANST (SEQ ID NO:1) was identified as vimentin, which is localized on the cell surface of tumor cells but not on normal cells. Vimentin expression in tumors is associated with the epithelial to mesenchymal transition and increased malignancy and metastasis in tumors. Lastly, this gene product-targeted approach minimized the risk of IL-12-induced toxicity. These results show the promise of using VNTANST (SEQ ID NO:1) to as a homing peptide to target therapeutic compounds to tumor cells, for example, to improve delivery of IL-12 treatments.

We have developed a fully functional tumor targeting IL-12 gene construct that can be delivered systemically for treating distally located neoplastic diseases. We have administered the peptide CHP-IL-12 by direct intravenous injection, and have directly injected the gene construct into tissue followed by electroporation. Inserting peptide-encoding sequences directly prior to the stop codon in the p40 gene of an IL-12 plasmid did not interfere with transcription, translation, post-translational modifications, or therapeutic functionality of the IL-12 gene product. Also, CHP maintained its tumor-targeting ability as seen in IL-12$^{-/-}$ mice and increased the therapeutic efficacy of systemic IL-12 gene-therapy treatments while decreasing liver toxicity. In fact, CHP-IL-12 may home or target the tumor better than CHP alone.

BRIEF DESCRIPTION OF THE DRAWINGS

FIG. 2A depicts the CHP-IL-12 construct with insertion of the CHP-coding sequence directly before the stop codon in the p40 subunit of IL-12 (arrow). CMV shows the location of the cytomegalovirus promoter; IVS shows the location of the intron; SEAP shows the location of the SEAP-coding sequence; STOP shows the location of the stop codon; and, pA shows the location of the bovine growth hormone polyadenylation signal.

FIG. 2B shows expression of IL-12 after in vitro transfection of 4T1 cells with control, wtIL-12, CDGRC-IL-12, and CHP-IL-12 (n=3).

FIG. 2C shows induction of IFN-γ from splenocytes after transfer of condition medium containing Control, wtIL-12, CDGRC-Il-12, or CHP-IL-12 gene products.

FIG. 2D shows IL-12 accumulation in tumor-bearing IL-12$^{-/-}$ mice treated with CHP-IL-12 or wtIL-12 determined via an IL-12p70 ELISA. Columns represent the wtIL-12-normalized level of IL-12/protein (pg/mg) in tumor per IL-12/protein (pg/mg) in kidneys, livers, and spleens and IL-12 pg/mL serum (n=4). Error bars represent the standard error of the mean (SEM) (* represent p<0.05 compared to all groups).

FIG. 3A shows tumor growth following treatments with CHP-IL-12, wtIL-12, and control plasmid DNA in 4T1 tumor-bearing balb/c mice (n=5; * represents p<0.05 at day 30 and p<0.001 from day 33 until day 42 compared to wtIL-12 plasmid DNA and p<0.01 at day 21 and p<0.001 from day 24 to day 33 compared to control plasmid DNA).

FIG. 3B shows metastatic nodules in the lungs of 4T1 tumor-bearing balb/c mice (n=5) treated with CHP-IL-12, wtIL-12, and control plasmid DNA and sacrificed 17 days after the second treatment (* represents p<0.05 compared to wtIL-12 plasmid DNA; # represents p<0.001 compared to control plasmid DNA).

FIG. 3C shows Kaplan-Meier survival analysis of the 4T1 tumor-bearing balb/c mice treated with CHP-IL-12, wtIL-12, and control plasmid DNA (* represents p<0.05 compared to wtIL-12 plasmid DNA; # represents p<0.001 compared to control plasmid DNA).

FIG. 11 shows the tumor volume in SCCVII tumor-bearing C3H mice at various days after inoculation with various gene constructs, each comprising the named peptide added to the p40 subunit of IL-12 prior to the stop codon.

MODES FOR CARRYING OUT THE INVENTION

Figure 1A:
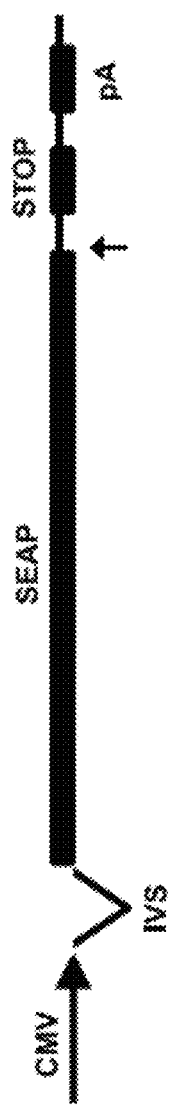
FIG. 1A depicts the peptide-SEAP (secreted alkaline phosphatase) constructs with insertion of the peptide-coding sequence directly before the stop codon (arrow). CMV shows the location of the cytomegalovirus promoter; IVS shows the location of the intron; pA shows the location of the bovine growth hormone polyadenylation signal; SEAP shows the location of the secreted alkaline phosphatase-coding sequence; STOP shows the location of the stop codon.

Tumor targeting can be achieved via the screening of various libraries to select tumor-targeted peptides, DNA/RNA aptamers, antibodies, and other known strategies. However, the only mechanism that can be used for homing gene products from systemically injected genes is the use of DNA sequences encoding for tumor-targeted mini-peptides. The small size of these peptides eliminates the concern of immunogenicity, as shown below, and reduces the effect on the biological function of the gene product, though some mini-peptides may boost or inhibit gene function [20]. The peptide-encoding DNA sequences can be easily fused with any therapeutic gene. Finally, the use of the mini-peptides can complement existing tumor targeting approaches such as transcriptional targeting, translational targeting, and targeted delivery].

We have discovered a tumor-targeting 7-amino-acid peptide, carcinoma homing peptide ("CHP," amino acid sequence of VNTANST (SEQ ID NO: 1)). The peptide VNTANST (SEQ ID NO:1) was previously reported to target normal lungs when present on the surface of virus particles [14]. We have shown that CHP was more effective than the known cyclic tumor-homing peptides such as CNGRC (SEQ ID NO:9) and RGD4C for targeting to tumors, which rely on disulfide bonds to maintain the cyclic structure of the targeting peptides.

Other tumor targeting peptides have been shown to deliver small molecules with only one copy for each small-molecule payload but require multiple copies of the peptide to target larger molecules such as a full length cytokine [24]. We have shown that fusion of a single copy of CHP-encoding DNA (gtcaacacggctaactcgaca (SEQ ID NO:2)) with the p40 subunit of IL-12 boosted the accumulation of IL-12 in tumors, suggesting one copy of CHP is sufficient to carry one copy of IL-12 to the tumor site.

Currently, most tumor-targeting strategies are based on extremely specific interactions, and the ability to target the tumor environment is constrained to a single cell type or specific type of tumor. We have shown, as discussed below, that CHP increased the efficacy of IL-12 gene therapy to inhibit tumor growth in the three tumor cell lines (i.e., breast adenocarcinoma, squamous cell carcinoma, and colon carcinoma), and in two different mouse strains. In addition, CHP-IL-12 extended survival more than wtIL-12 treatments in both the breast adenocarcinoma and squamous cell carcinoma cell lines. Similarly, CHP-IL-12 treatments inhibited the development of spontaneous lung metastasis, which is the primary killer of cancer patients. This increase in anti-tumor response was associated with increases in both tumor-specific cytotoxic T lymphocyte (CTL) activity and IL-12 accumulation in tumors. This result was in agreement with the result that intratumoral delivery of IL-12 yields better anti-tumor efficacy than systemic delivery [7]. The discovery of CHP is important since it will allow for systemic delivery to target IL-12 to tumors without the need of intratumoral delivery, which is not realistic for treating internal tumors, metastatic tumors, and residual tumor cells after standard therapy.

We also identified vimentin as a cell receptor for CHP. Vimentin is an intermediate filament protein conventionally regarded as an intracellular structural protein in cells of mesenchymal origin such as fibroblasts, chondrocytes, and macrophages [15]. Vimentin expression has been reported to be increased in several tumor models, including human prostate, colon [17], hepatocellular [16], and gemcitabine-resistant pancreatic cancers[19], and the tumor stromal cells in human colorectal tumors [18]. The upregulation of vimentin is associated with the epithelial-to-mesenchymal transition (EMT), which is important for motility as well as metastasis in several tumors. In addition, vimentin was recently discovered to be expressed on the cell surface of tumor cells [25] and epithelial cells during angiogenesis [26]. Additionally, some human tumor-initiating cells remaining after treatment overexpress vimentin on the tumor cell surface [27]. Another important aspect of vimentin is the conserved sequences among mouse, rat, dog, and humans [28]. This information along with our result for the tumor/serum SEAP accumulation in the xenogeneic human tumor model indicates that CHP targeting will be effective in human treatments.

We also confirmed (as discussed below) that vimentin is expressed at very low levels in the heart, liver, kidney, spleen, and serum of C3H mice, yet it is highly expressed in lung tissue. However, since most general expression of vimentin is intracellular [15, 29, 30], this expression should not be a target of CHP. We found that there was no accumulation of CHP-biotin in the lung sections which supports this theory. Conversely, as shown below, vimentin is highly expressed in aggressive murine squamous cell carcinoma (SCCVII) tumors in C3H mice, and CHP-biotin accumulated in the SCCVII tumors. Likewise, the tumor cells and corresponding syngeneic tumors both expressed detectable levels of vimentin. The differences seen between expression in tumor cell lines and the respective tumor tissues was due to the heterogeneous nature and multiple cell types in the tumor microenvironment.

We have developed a fully functional tumor-targeting IL-12 p40 gene construct based on CHP that can be delivered systemically for treating distally located neoplastic diseases. Inserting peptide-encoding sequences directly prior to the stop codon in the p40 subunit gene of an IL-12 plasmid did not interfere with transcription, translation, post-translational modifications, or therapeutic functionality of the IL-12 gene product. Also, CHP maintained its tumor-targeting ability as seen in IL-12-/- mice and increased the therapeutic efficacy of systemic IL-12 gene-therapy treatments, while decreasing liver toxicity. CHP-IL-12 was found to be more effective in decreasing tumor growth than other mini-peptides linked to the same p40 subunit of IL-12.

The term "CHP" used herein and in the claims refers to the peptide VNTANST. The term "CHP analogs" is understood to be peptides with consecutive sequences of 3 or more amino acids from VNTANST (SEQ ID NO:1) and that exhibit a qualitatively similar effect to the unmodified VNTANST (SEQ ID NO:1)peptide. Based on the effective size of other mini-peptides, we believe that effective CHP analogs include any three or greater consecutive amino acid sequence found within the CHP sequence, more preferably any four or greater consecutive amino acid sequence found within the CHP sequence, and most preferable any five or six consecutive amino acid sequence found within the CHP sequence. In addition, any DNA sequence that codes for any of the above VNTANST (SEQ ID NO:1)sequence or CHP analog sequences can be used for making tumor targeting constructs. In the experiments below, we used the DNA sequence of gtcaacacggctaactcgaca (SEQ ID NO:2) to encode for CHP, but due to the degeneracy of the DNA code, any DNA sequence that would code for CHP could be used. In addition, any DNA sequence that encodes for the CHP analogs could be used. CHP or CHP analog may be a synthetic or recombinant peptide. With its specific tumor targeting property, CHP peptide or CHP analogs or the DNA encoding for CHP or CHP analogs can carry therapeutic proteins, peptides, drugs, genes, cells, viral or nonviral vectors, bacteria and other modalities into tumor tissues, reducing the toxicity to other organs and increasing the therapeutic efficacy. As a result, a low dose of the peptide or construct may be needed for treating tumors. CHP or CHP analogs or the corresponding DNA encoding for CHP or CHP analogs can also be used to carry therapeutic agents for prevention or treatment of metastatic tumors. Therapeutic agents are well known in the art (e.g., peptides, chemotherapeutic agents, liposomes, nanoparticles) that can be conjugated to a targeted peptide for increased accumulation of the therapeutic agent in the tumor environment.

CHP and CHP analogs can be used in a variety of applications including exploratory studies to diagnose tumors or tumor metastasis in combination with image tools, to monitor the effect of treatments in combination with image tools, and to deliver therapeutic agents for treating metastatic tumors and tumors localized in internal organs as well as prevent tumor recurrence from residual tumors after standard therapy. The therapeutic agents to be carried by CHP and CHP analogs include anti-tumor drugs, peptides, proteins, genes, cells, viral/nonviral vectors, bacteria and others. For example, the p40 subunit of the protein IL-12 was used below. We have made a new conjugate of CHP and the p40 subunit of IL-12. The sequence of this new construct is found in Table 1, below. The peptide sequence for CHP-IL-12 is SEQ ID NO: 3, and the nucleic acid sequence is SEQ ID NO: 4. Initial work on conjugating other cytokines to CHP, for example IL-15 and PF4, indicate that some increase in efficacy was seen for IL-15, but that in these initial tests, no increase in efficacy was seen in CHP-PF4.

CHP and CHP analogs can be administered by methods known in the art. In our work, we have used both direct injection of the gene construct into tissue followed by electroporation, and have directly injected the peptide intravenously. As a DNA gene construct, the delivery can be from vectors which may be derived from viruses or from bacterial plasmids. There are many methods to deliver gene constructs to tumors or targeted tissues. Some examples of the various delivery systems can be found in U.S. Pat. Nos. 5,910,488; 7,192,927; and 7,318,919; whose descriptions of such delivery systems are hereby incorporated by reference. In addition, the vector delivery system may incorporate a promoter sequence to initiate transcription of the gene construct.

TABLE 1

| Peptide and Conjugate | | |
|---|---|---|
| SEQ ID NO: 1 | VNTANST | Peptide (CHP) |
| SEQ ID NO: 2 | gtcaacacggctaactcgaca | DNA Coding for CHP |
| SEQ ID NO: 3 | MCPQKLTISWFAIVLLVSPLMAMWELEKDVYVVEVDWTPDA PGETVNLTCDTPEEDDITWTSDQRHGVIGSGKT LTITVKEFL DAGQYTCHKGGETLSHSHLLLHKKENGI WSTEILKNFKNKTF LKCEAPNYSGRFTCSWLVQRNMD LKFNIKSSSSSPDSRAV TCGMASLSAEKVTLDQRDYE KYSVSCQEDVTCPTAEETLP IELALEARQQNKYENYSTSFFIRDIIKPDPPKNLQMKPLKNSQ VEVSWEYPDSW STPHSYFSLKFFVRIQRKKEKMKETEEGC NQKGAFLV EKTSTEVQCKGGNVCVQAQDRYYNSSCSKWA CVPCRVRSVNTANSTKL* | CHP-IL-12 Peptide |
| SEQ ID NO: 4 | atgtgtcctcagaagctaaccatctcctggtttgccatcgttttgctggtgtctccactcat ggccatgtgggagctggagaaagacgtttatgttgtagaggtggactggactcccga tgccctggagaaacagtgaacctcacctgtgacacgcctgaagaagatgacat cacctggaccctcagaccagagacatggagtcataggctctggaaagaccctgacc | DNA Coding for CHP-IL-12 |

TABLE 1-continued

Peptide and Conjugate

```
atcactgtcaaagagtttctagatgctggccagtacacctgccacaaaggaggcgag
actctgagccactcacatctgctgctccacaagaaggaaaatggaatttggtccac
tgaaattttaaaaaatttcaaaaacaagactttcctgaagtgtgaagcaccaaattactc
cggacggttcacgtgctcatggctggtgcaaagaaacatggacttgaagttcaacatc
aagagcagtagcagttcccctgactctcgggcagtgacatgtggaatggcgtctctgt
ctgcagagaaggtcacactggaccaaagggactatgagaagtattcagtgtcctgc
caggaggatgtcacctgcccaactgccgaggagaccctgcccattgaactggcgtt
ggaagcacggcagcagaataaatatgagaactacagcaccagcttcttcatcagg
gacatcatcaaaccagacccgcccaagaacttgcagatgaagcctttgaagaactc
acaggtggaggtcagctgggagtaccctgactcctggagcactccccattcctacttc
tccctcaagttctttgttcgaatccagcgcaagaaagaaaagatgaaggagacaga
ggaggggtgtaaccagaaaggtgcgttcctcgtagagaagacatctaccgaagtcc
aatgcaaaggcgggaatgtctgcgtgcaagctcaggatcgctattacaattcctcgtg
cagcaagtgggcatgtgttccctgcagggtccgatccgtcaacacggctaactcgac
aaagctttga
```

Example 1

Materials and Methods

Plasmid DNA Preparation.

All SEAP gene constructs were generated via direct PCR as previously described [13]. The wild type IL-12 gene construct (wtIL-12) was obtained from Valentis, Inc. (San Francisco, Calif.) [34], and gene sequences encoding the peptide sequences were inserted directly prior to the stop codon of the IL-12 p40 subunit encoding region using the primer sequences listed in Table 2, below. The wtIL-12 plasmid includes both the p35 and p40 subunits. The control plasmid DNA (control) consisted of a deletion of the IL-12 gene from the IL-12 construct. All plasmid DNAs were manufactured with the Qiagen (Alameda, Calif.) EndoFree plasmid preparation kit.

Cell Lines, In Vitro Gene Transfer, and IFN-γ Induction.

CT26 (colon cancer), SCCVII (squamous cell carcinoma), 4T1 (breast carcinoma), EMT6 (breast cancer), and B16F10 (skin melanoma) cell lines were obtained from American Type Culture Collection (ATCC, Manassas, Va.), the AT84 (squamous cell carcinoma) cell line was a generous gift from Dr. Edward Shillitoe (State University of New York Upstate Medical School), and MCF7 (xenogeneic human breast cancer) cells were provided by Dr. Bolin Liu (University of Colorado Denver School of Medicine). All cell lines were maintained in Dulbecco's modified Eagle's medium containing 10% fetal bovine serum (DMEM) (Life Technologies, Carlsbad, Calif.) at 37° C. and 5% $CO_2$.

For in vitro transfections, 4T1 cells were suspended at a concentration of $1 \times 10^7$ cells/mL Opti-mem medium (Life Technologies), and 100 μL of this suspension were transferred to individual electroporation cuvettes and 2 μg of Control, wtIL-12, CDGRC-IL-12, or CHP-IL-12 plasmid DNA was added (n=3). Each cuvette was pulsed with one 75-ms pulse of 150 V, and the suspensions were transferred to individual wells of a 6-well plate containing 900 μL DMEM. The next day, 900 μL of medium was collected, placed on ice, and analyzed for the presence of IL-12p70 using an IL-12p70 ELISA (eBiosciences, San Diego, Calif.) as per the manufacturer's instructions. The spleen from a naïve Balb/c mouse was placed in serum-free RPMI-1640 containing Pen/Strep/Glu (RPMI), splenocytes were filtered through a 70 μm cell strainer, and suspended in 10 mL RPMI. After the cell suspension was centrifuged for 10 minutes at 1,000 rpm, the supernatant was removed, cells resuspended in 10 mL red blood cell (RBC) lysis solution, centrifuged again, and then resuspended in RPMI at a concentration of $2 \times 10^6$ cells per 100 μL. $2 \times 10^6$ cells were placed into wells of a 6-well plate. Condition medium from the plasmid DNA-transfected cells containing 150 μg/mL IL-12 was transferred to these wells and the volume was adjusted to 1 mL with DMEM. The next day, the mediums were collected and assayed for the presence of IFN-γ using an IFN-γ ELISA (eBiosciences) as per manufacturer's instructions.

Animal Models, Tumor Inoculations, In Vivo Gene Transfer, Protein Extraction, and Therapeutic Analyses.

All animals used in this study were maintained under and animal protocols were performed following National Institutes of Health guidelines, approved by the Institutional Animal Care and Use Committee (IACUC) of Louisiana State University (Baton Rouge, La.). Balb/c mice were obtained from the in-house breeding colony, and C3H, Nude, and wtIL-12$^{-/-}$ mice were obtained from Charles River Laboratories (Wilmington, Mass.). All mice were six to eight weeks old upon initiation of experiments. Tumor models were initiated via subcutaneous inoculations of 30 μL cell suspension containing $1 \times 10^5$ 4T1 cells or $2 \times 10^5$ cells for all other cell lines in 1×PBS. Orthotopic EMT6 tumors were initiated by inoculating $1 \times 10^5$ cells in the mammary fatpads of female Balb/c mice.

For in vivo i.m gene transfections, plasmid DNA was diluted in 0.45% NaCl to a concentration of 5 μg/30 μL, 30 μL was then injected into each rear tibialis muscle, and the muscles were immediately subjected to electroporation (EP) as previously described [20]. When 4T1 tumors were 3 to 4 mm in diameter or all other tumor models were 4.0 to 4.5 mm in diameter, the first treatment was performed, and a second identical treatment was performed 10 days later. Tumor volumes were determined as previously described [13]. To determine the distribution of the fusion gene products peptide-SEAP and peptide-IL-12, the treatments were performed when tumors reached 6-7 mm in diameter; 72 hours after treatment, mice were sacrificed via $CO_2$ asphyxiation; and then tissues were collected, wrapped in foil, and flash-frozen in liquid nitrogen. To extract proteins, the frozen tissues were smashed with a hammer, placed in 1× lysis buffer (Promega, Madison, Wis.), beaten for 1 minute with a mini-beadbeater 8 (Biospec, Bartlesville, Okla.), and spun at 16,000×g for 5 minutes. The supernatant was transferred to a new tube. Serum was collected by extracting blood from the left ventricle, transferring it to Serum Separator Tubes (BD, Franklin Lakes, N.J.), and spinning at 5,000×g for 5 minutes. The serum was then transferred to a new 1.5 mL tube.

India ink inflation was performed to determine the level of lung metastasis. After $CO_2$ asphyxiation, the thoracic cavity was opened, the trachea exposed, and the trachea clipped with a hemostat. 1.5 mL 15% India ink was injected into the lung which was then transferred into 20 mL Fekete's solution and incubated overnight. The next day, white metastatic nodules were counted using a dissecting microscope.

For fluorescence-activated cell sorting (FACS) analyses, tumor infiltrating lymphocytes were isolated by extracting the tumors, cutting them into pieces, and resuspending the mixture in sterile PBS (without $Ca^{2+}$ and $Mg^{2+}$) containing a mixture of collagenase IV, hyaluronidase V (Sigma-Aldrich, St. Louis, Mo.), and DNase II (Fisher, Pittsburgh, Pa.). The tissue suspension was placed in a shaker at 37° C. for 1-2 hours, and then poured through a 70 μm cell strainer, followed by washing twice in PBS with $Ca^{2+}$ and $Mg^{2+}$. The isolated cells were stained with the fluorescein isothiocyanate (FITC) conjugated anti-CD11c (AbD Serotec, Raleigh, N.C.) and goat anti-mouse CD80 (R&D, Minneapolis, Minn.) for 30 min at 4° C., washed with PBS, and then stained with R-Phycoerythrin (PE) conjugated anti-goat IgG (Cedarlane Laboratories, Burlington, N.C.). The expression of the proteins was analyzed on FACS Calibur (BD Biosciences, San Jose, Calif.) and analyzed with FCS Express 3 (De Novo Software, Los Angeles, Calif.). Splenocytes were also isolated from Balb/c mice bearing orthotopic EMT6 tumors, and a CTL assay was performed as described previously[13]. Serum was collected from 4T1-tumor bearing mice 3 days after treatments with Control, wtIL-12, and CHP-IL-12 plasmid DNA as described above. The serum was analyzed for the presence of IFN-γ as described above.

Peptide-Biotin Distribution, Vimentin Depletion, and Tissue Staining.

CHP-biotin was synthesized by United Biochemical Research, Inc. (Seattle, Wash.) at >95% purity, resuspended in $H_2O$ with 5% glycerol, and stored at −80° C. The peptide sequence is $NH_2$-VNTANSTGG (SEQ ID NO:28)-biotin. Control-biotin was created by conjugating a non-specific peptide (CTSTSPLPPPSHSTSKKG (SEQ ID NO:29), Alpha Diagnostics, San Antonio, Tex.) to EZ-Link Amine-PEG2-Biotin via 1-Ethyl-3-(3-dimethylaminopropyl) carbodiimide (EDC) cross-linking (Pierce, Rockford, Ill.) following the manufacturer's instructions. The peptide-biotin conjugates (10 μg/100 μL normal saline) were injected into the tail vein of C3H mice bearing SCCVII tumors with 6-7 mm diameters. For vimentin depletion studies, goat polyclonal anti-vimentin (Millipore, Billerica, Mass.) was purified via protein-G antibody purification (Pierce), and 150 μg was added to the peptide-biotin conjugate solutions for administration. One hour after intravenous (i.v.) administration, mice were perfused via injection of 10 mL 1×PBS into the left ventricle after cutting the right atrium. The tissues were immediately removed, wrapped in foil, and flash frozen in liquid nitrogen. Four- to five-micron sections were placed on poly-L-lysine coated slides.

The sections were fixed in ice-cold acetone, non-specific interactions were blocked with 1% BSA (bovine serum albumin) in PBS (phosphate buffered saline), and endogenous peroxidase activity was suppressed with Stable peroxidase suppressor (Pierce). Since the peptides already contained biotin, the peptide were incubated with the avidin-HRP reagent Vectastain ABC (Vector Biolabs, Philadelphia, Pa.) for 45 minutes, washed in PBS, and then incubated with 1× Metal Enhanced DAB (Pierce). The sections were then counter-stained with Meyer's hematoxylin (blue) for 2 minutes or eosin (pink) for 20 seconds.

Isolation of Cell-Surface Proteins, Identification of CHP Receptor, and Western Blot.

Cell surface proteins were isolated from SCCVII cells by using the Cell Surface Protein Isolation Kit (Pierce) and following the manufacturer's instructions. A streptavidin agarose column (Peirce) was loaded with CHP-biotin (3 mg/mL in PBS for 10 in), and the cell surface protein suspension was incubated on the column overnight at RT. Next, five fractions were eluted with 8 mol/l Guanidine-HCl, pH 1.5, and then 1 mol/l $Na_2$ $HPO_4$ was added to the fractions at a 1:10 ratio. From these fractions, volumes containing 40 μg of protein were mixed with 2× sodium dodecyl sulfate (SDS) loading buffer and added to wells of a 12% polyacrylamide gel and an electric field was applied. The gel was then incubated with Coomassie Brilliant Blue R250 followed by destaining solution (10% Acetic Acid and 20% MeOH). Images were captured with a VersDoc Model 1000 and Quantity One Version 4.4.1 software (BioRad, Hercules, Calif.).

To identify the protein from fraction two, the protein in the gel was extracted using the Trypsin Profile IGD Kit (Sigma, St. Louis, Mo.) with the ProteoPrep Reduction and Alkylation Kit (Sigma) following the manufacturer's instructions. Liquid chromatography electrospray tandem mass spectrometry (LC MS/MS) was used to analyze peptide mixture extracted from gel spots. Tryptic digests of gel spots (~6 μl) were diluted with 0.1% formic acid (10 μl) and 10 μl injected by microplate autosampler (Famos, Dionex Corporation, Sunnyvale, Calif.) onto a 0.3×1 mm trapping column (PepMap C18, Dionex Corporation) using a nano LC system equipped with Switchos and Ultimate 2000 pumps (Dionex Corporation), at a flow rate of 10 μl/min. The Switchos valve was set on loading position prior to sample loading. After sample loading, the trapping column was washed with 0.1% formic acid at flow rate of 5 ul/min for additional 5 min and then switchos valve was switched to inject position. Peptides were then eluted at 200 nl/min and chromatographed on a 75 μm×15 cm Biobasic C18 column (Vydac HPLC Columns, Grace Davison, Ill.), with a gradient of 5-40% acetonitrile over 60 min followed by 80% acetonitrile for 5 min. The eluent was directed into a quadrupole time-of-flight mass spectrometer (Q-Star, Applied Biosystems MDS Sciex) and ionized immediately using electrospray source (Nano spray II, Applied Biosystems MDS Sciex) at high voltage of 2.5 kv with nebulizer gas at level 2. The mass spectrometer was operated in IDA (information dependent acquisition) mode with the three most intense ions in each survey scan subjected to MS/MS analysis using collision energies ranging from 20 eV to 50 eV. MS/MS data obtained from Q-Star was processed for database search using Mascot search engine (Matrix science, UK). A Mascot search was performed using the following parameters: type of search, tandem mass spectrometry ion search; database, nrNCBI; taxonomy, all; enzyme, trypsin; fixed modification, carbamidomethyl (C); mass values, monoisotopic; protein mass, unrestricted; peptide mass tolerance, +0.2 Da; fragment mass tolerance, +0.2 Da; and maximum miss cleavage, 1.

A cell-free assay was developed to confirm that vimentin interacts with CHP. Wells of a microtiter plate were coated with 50 μL of 100 mmol/l $NaHCO_3$ (coating buffer) or 5 μg/mL of either vimentin-GST or GST (ProSpec, East Brunswick, N.J.) in coating buffer and incubated at 4° C. overnight. After 2 washes with PBS, non-specific binding was blocked by incubating the wells with 100 μL 1×BSA for 2 hours at room temperature. After another wash (twice), 100 μL of PBS containing 10 ng CHP-biotin was added to each well (n=6 for each coat), incubated for 2 hours at room temperature, and then washed 4 times with PBS. Avidin-HRP (100 µL, eBiosciences) was added to each well, incubated for 30 minutes, and the wells were washed 7 times with PBS. Lastly, 100 µL TMB substrate (eBiosciences) was added to each well for 15 min followed by 50 µL Stop solution (eBiosciences), and the absorbance at 450 nm was read using a SpectraCount and PlateReader Version 3.0 software (PerkinElmer, Waltham, Mass.).

To prepare cells for western blot analysis of cellular expression of vimentin, when SCCVII, CT26, 4T1, and B16F10 cells were 95% confluent in individual wells of 6-well plates, the cells were directly lysed with 60 µL Laemmli sample buffer. For preparation of ex vivo samples, tissues and tumors were processed as described above. Volumes of the tissue lysates containing 40 µg of protein were mixed with 2×SDS loading buffer. Twenty microliter volumes of the cell lysates or tissue lysates were added to a 12% polyacrylamide gel and subjected to SDS-PAGE and then transferred to a TransBlot Transfer Medium nitrocellulose membrane (Bio-Rad Laboratories). Immunoblotting of the membrane was performed with a 1:100 dilution of polyclonal Goat anti-vimentin (Millipore) and a 1:5,000 dilution of the secondary horseradish peroxidase conjugated rabbit anti-goat IgG. The peroxidase signal was generated with the Western Lightning ECL (PerkinElmer) and visualized with a Kodak Image Station 440CF using the 1D Image Analysis Software v3.6 (PerkinElmer).

Analysis of Toxicity Induced by Gene Therapy Treatments.

SCCVII tumors were induced in C3H mice as described above, and allowed to grow to a volume of 300 mm$^3$. Groups of four mice for each treatment at each time point were treated with either wild-type IL-12 or CHP-IL-12 as described above at a dose of 1 µg, 2 µg, and 10 µg plasmid DNA; a fourth set of mice received 3 treatments of 2 µg. Mice were sacrificed on days 1, 3, and 30 after the second treatment, blood was collected in serum separator tubes, and livers were fixed in 10% neutral-buffered formalin.

Serum chemistry profiles were analyzed by a private GLP-certified diagnostic laboratory (Antech Diagnostics, Memphis, Tenn.). Formalin-fixed tissue was cut-in, embedded in paraffin, and sectioned into 5 µm sections. Sections were mounted on glass slides and stained with hematoxylin and eosin prior to microscopic examination by a pathologist. A liver toxicity scoring system based on the number of characteristic liver lesions (foci of hepatocellular necrosis with Kupffer cell hyperplasia) per 200× field was used. The sections were scored blindly and recorded for analysis.

Statistical Analyses

All statistical analyses were performed with GraphPad Prism version 5.00 for Windows, (GraphPad Software, San Diego, Calif.). One-way ANOVA with Bonferroni's post-hoc test was used to analyze the following data: ratios of Tissue/Serum (T/S) SEAP levels, production of fusion gene products from in vitro transfected 4T1 cells, inhibition of metastasis, IFN-γ serum levels, and CHP/vimentin interaction. Tumor versus normal tissue distributions of exogenous IL-12 or CHP-IL-12 gene products in IL-12$^{-/-}$ mice and CTL data were analyzed via one-tailed unpaired T tests. All tumor growth experiments were analyzed via two-way ANOVA plus Bonferroni's post-hoc test. Mantel-Cox tests were used to analyze differences in survival of mice. Liver toxicity was first analyzed using blind pathological scores of the liver tissues, but no differences were seen among time points, so the data was pooled to create a larger sample size and then analyzed with one-sided Fisher's exact tests comparing the number of mice having lesions from CHP-IL-12 and wtIL-12 fusion plasmid DNA treated mice.

CHP-Antibody Assay.

To determine if CHP causes the production of CHP-specific antibodies, wells of a polystyrene plate were coated with coating buffer only, control peptide (CTSTSPLPPP-SHSTSKKG (SEQ ID NO: 29)), or CHP, washed, and blocked as described above. Next, 20 µL of serum from EMT6 tumor-bearing Balb/c mice 30 days after being treated twice 10 days apart with control, wtIL-12, or CHP-IL-12 plasmid DNAs were added to the wells, and 10×, 100×, and 1000× dilutions of serum were added to more CHP-coated wells (n=3) and incubated at room temperature for 2 hours. The wells were washed 4 times with PBS, and then 1:500 biotin-conjugated goat antimouse IgG (Sigma Aldrich) was added to each well at room temperature for 1 hour. The presence of IgG was visualized with avidin-HRP/TMB coloring as described in Materials and Methods.

Vimentin-Bound CHP-IL-12 Activity Assay.

Wells of a polystyrene plate were coated with vimentin or BSA as described above. CHP-IL-12 and wtIL-12 produced from transfected Hela cells were transferred to the coated wells in a 1:1 molar ratio of vimentin and BSA coated on the wells. One hour later, splenocytes from mice were transferred to each well. Two days later, the medium was collected and analyzed via an IFN-γ ELISA as described above.

TABLE 2

| Peptide | Forward Primer 5'-3' | Reverse Primer 5'-3' |
|---|---|---|
| Primers for SEAP Constructs | | |
| SEQ ID NO: 5 CGFELETC | SEQ ID NO: 14 CCAGGATCCTAAAAGG GCAG | SEQ ID NO: 17 TTATCACTCGAGGCAAGTCTCTAGCTCGAATC CACATGTCTGCTCGAAGCGGCC |
| SEQ ID NO: 6 NGYEIEWYSWV THGMY | SEQ ID NO: 14 CCAGGATCCTAAAAGG GCAG | SEQ ID NO: 18 TTATCAGTACATACCGTGAGTAACCCAGGAGT ACCACTCGATCTCGTAACCGTTTGTCTGCTCG AAGCGGCCGG |
| SEQ ID NO: 7 TAASGVRSMH | SEQ ID NO: 14 CCAGGATCCTAAAAGG GCAG | SEQ ID NO: 19 TTATCAATGCATACTACGGACACCACTAGCAG CAGTTGTCTGCTCGAAGCGGCCGG |
| SEQ ID NO: 8 ATWLPPA | SEQ ID NO: 14 CCAGGATCCTAAAAGG GCAG | SEQ ID NO: 20 TTA TCAAGCTGGA GGGAGCCACG TAGCTGTCTG CTCGAAGCGG CCGG |
| SEQ ID NO: 9 CNGRC | SEQ ID NO: 14 CCAGGATCCTAAAAGG GCAG | SEQ ID NO: 21 TTATCAACAACGACCGTTACATGTCTGCTCGA AGCGGCCGG |

TABLE 2-continued

| Peptide | | Forward Primer 5'-3' | | Reverse Primer 5'-3' | |
|---|---|---|---|---|---|
| SEQ ID NO: 10 | HTMYYHHYQHHL | SEQ ID NO: 14 | CCAGGATCCTAAAAGGGCAG | SEQ ID NO: 22 | TTATCAAAGGTGATGCTGATAGTGATGGTAATACATAGTGTGTCTGCTCGAAGCGGCCGG |
| | GSL | SEQ ID NO: 14 | CCAGGATCCTAAAAGGGCAG | SEQ ID NO: 23 | TCGTCTAGATTATCACAGACTTCCACCCGGGTGCGCGGCGTCG |
| SEQ ID NO: 11 | NSSRGLG | SEQ ID NO: 14 | CCAGGATCCTAAAAGGGCAG | SEQ ID NO: 24 | TTATCAACCGAGATCCCTACTGCTGTTTGTCTGCTCGAAGCGGCC |
| SEQ ID NO: 12 | CDCRGDCFC | SEQ ID NO: 14 | CCAGGATCCTAAAAGGGCAG | SEQ ID NO: 25 | TTATCAGCAGAAACAATCACCGCGGCAATCACA |
| Primers for IL-12 Constructs | | | | | |
| SEQ ID NO: 1 | VNTANST | SEQ ID NO: 15 | GTCGACCCCGCCCAAGAACTTGCAG | SEQ ID NO: 26 | ACTAGTTTATCAAAGCTTTGTCGAGTTAGCCGTGTTGACGGATCGGACCCTGCAGGGA |
| SEQ ID NO: 13 | CDGRC | SEQ ID NO: 16 | GTTCGAATCTGCGATGGAAGATGCCAGCGCAAGAAAGAAAAG | SEQ ID NO: 27 | GAACAAAAGCTGGTACCGG |

Example 2

Figure 7A:
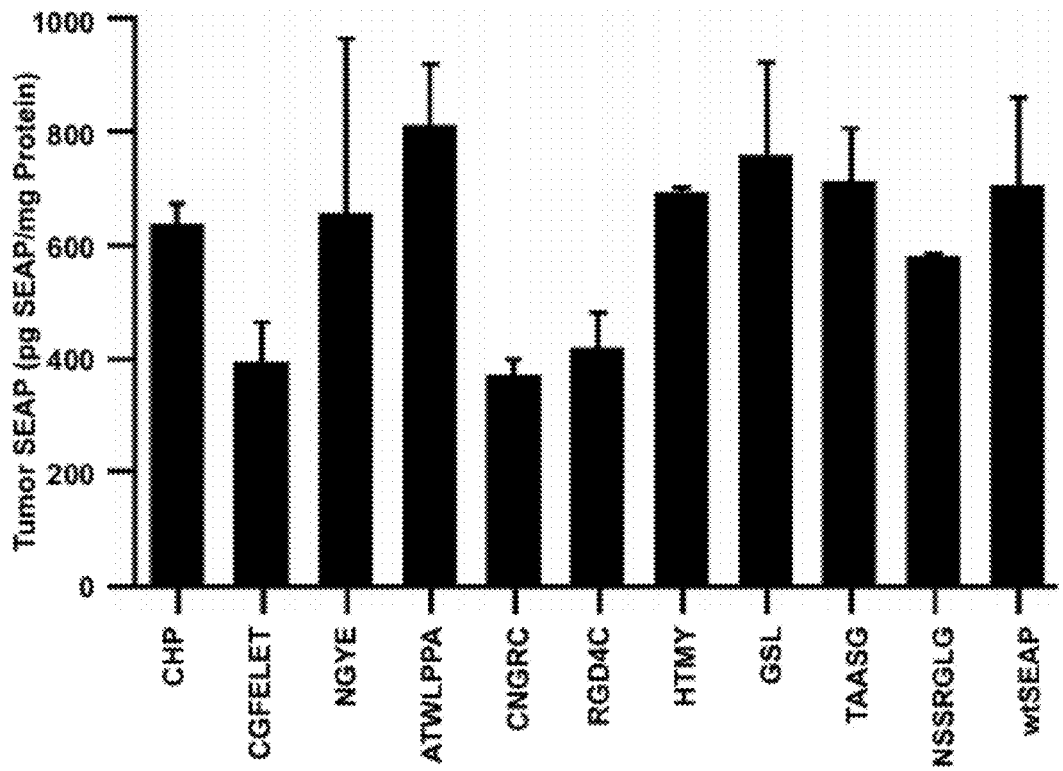
FIG. 7A shows SEAP activities in the tumors of the same CT26-tumor bearing mice used in FIG. 1B after peptide-SEAP plasmid DNA intramuscular electroporation of several peptides.
Figure 7B:
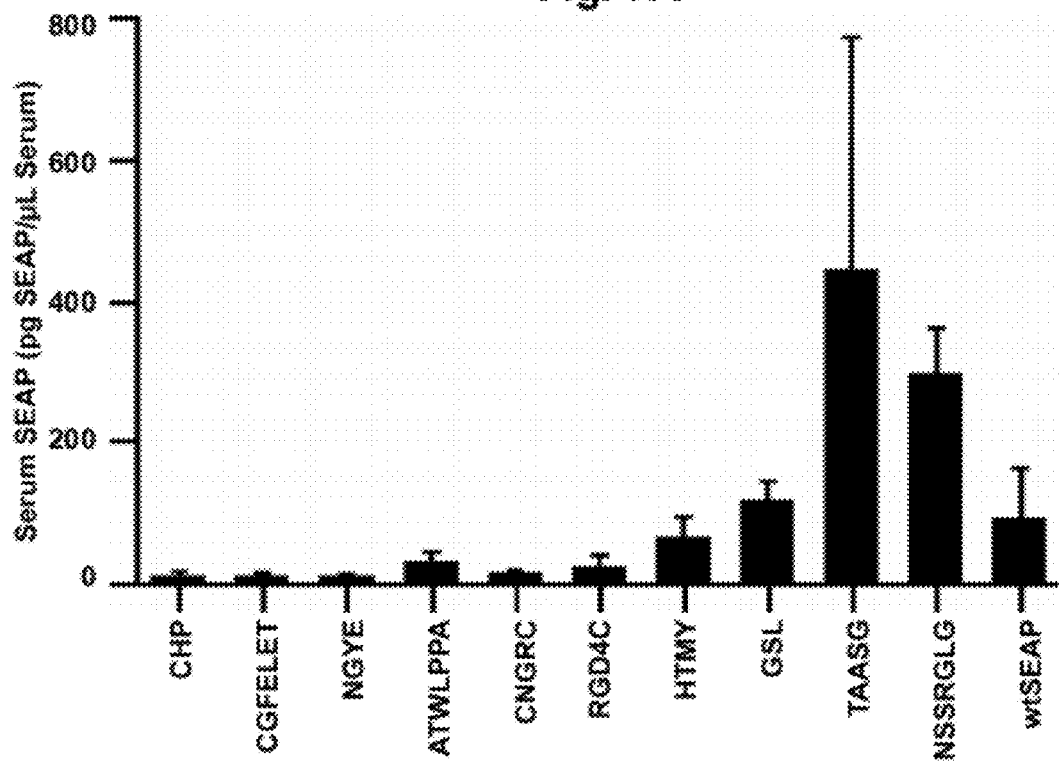
FIG. 7B shows SEAP activities in the serum of the same CT26-tumor bearing mice used in FIG. 1B after peptide-SEAP plasmid DNA intramuscular electroporation of several peptides.

CHP Increases Accumulation of the Fusion Reporter Gene Product and Biotin-CHP Conjugate into Tumors Several fusion gene constructs were cloned by inserting peptide encoding DNA sequences directly prior to the stop codon in a secreted alkaline phosphatase (SEAP) reporter plasmid DNA (FIG. 1A) using primers of Table 2 [13]. These peptide-SEAP fusion gene constructs were delivered via intramuscular (i.m.) electroporation (EP) of the anterior tibialis muscles in mice bearing tumors located 1 cm craniodorsal of the tail. After 72 hours, tumors and serum were collected and analyzed for SEAP distribution. It has been shown that inserting peptides into the SEAP plasmid can alter SEAP activity but not protein production [20]. To compensate for the altered SEAP activity, we used the ratio of the SEAP activity between tumors and serum (T/S SEAP). The un-corrected values for the tumor and serum SEAP activities are shown in FIG. 7A and FIG. 7B.

Figure 1B:
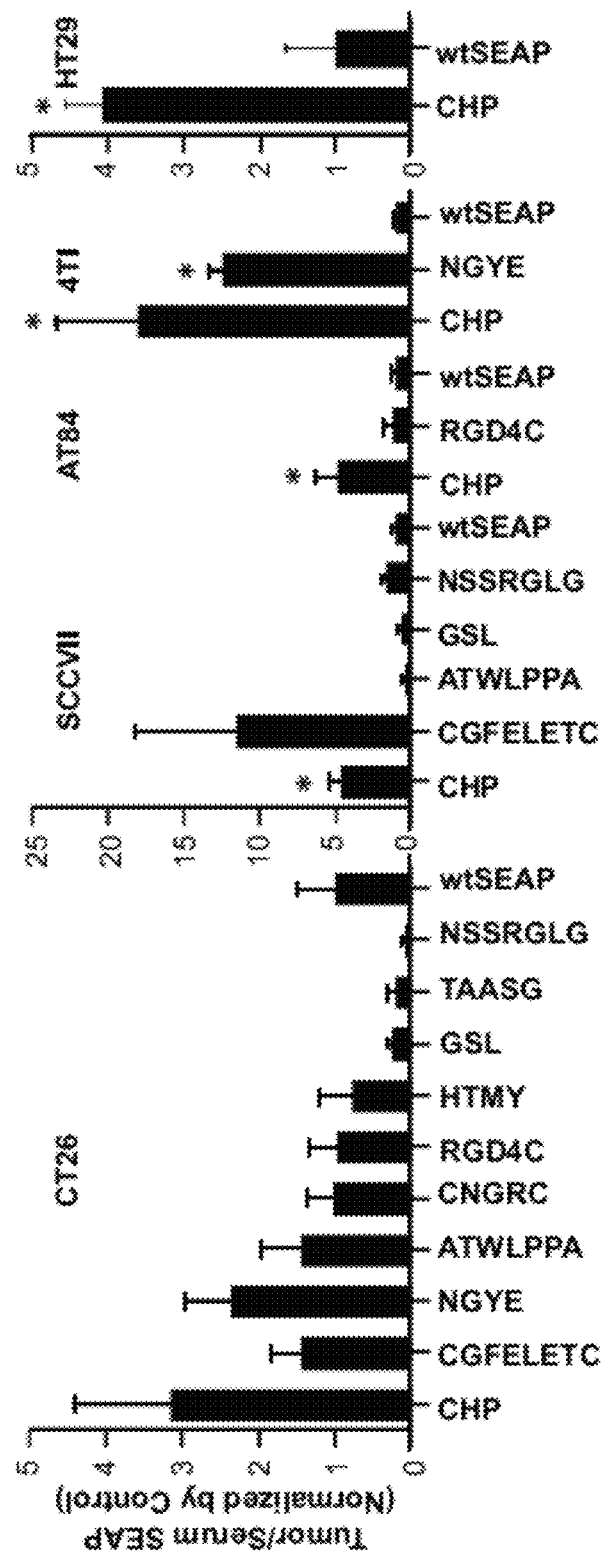
FIG. 1B shows T/S SEAP (ratio of the SEAP activity between tumors and serum) levels 72 hours after i.m. EP of several peptide-SEAP plasmid DNAs in syngeneic CT26 (n=3), SCCVII (n=4), AT84 (n=4), and 4T1 (n=4) tumor-bearing mice, as well as xenogeneic MCF7 (n=4) tumor-bearing mice.
Figures 1C, 1D:
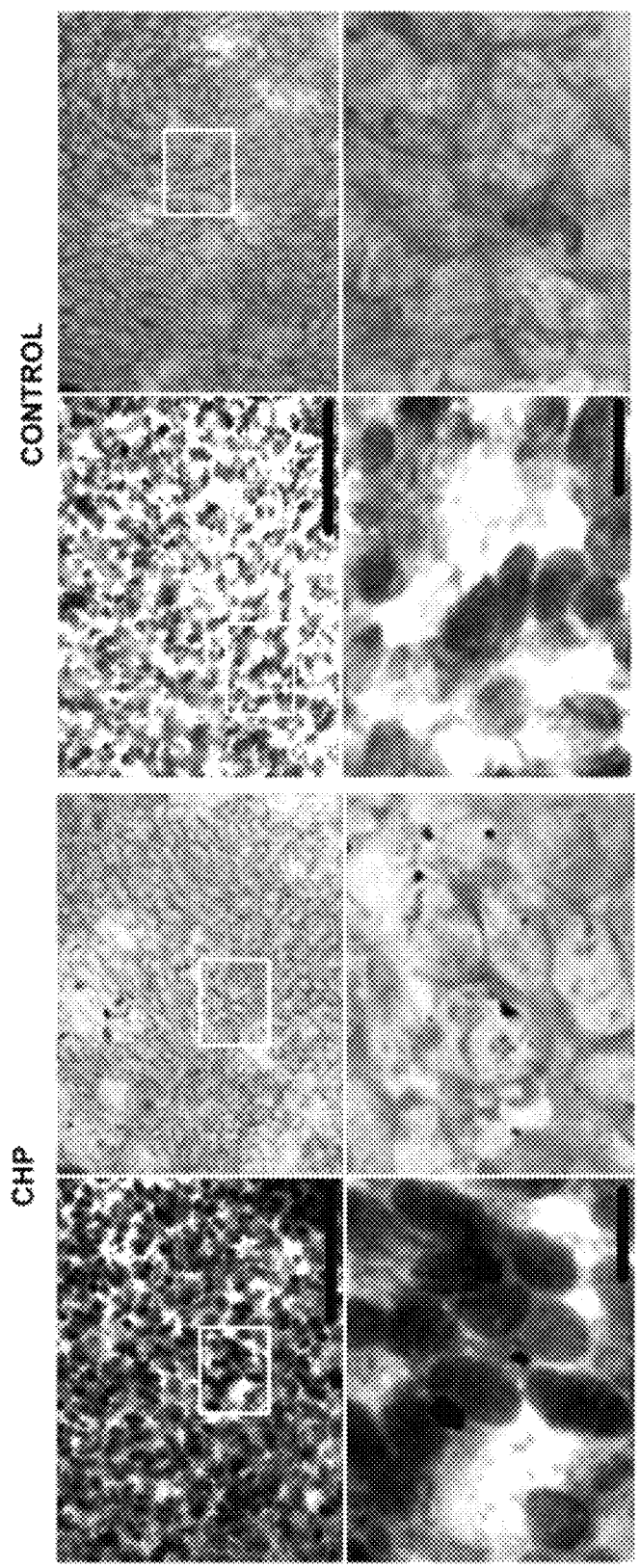
FIG. 1C shows DAB (diaminobenzidine) staining of tumor tissues from CHP-biotin treated mice counterstained with either hematoxylin (left) or eosin (right). The bottom images are larger versions of the areas within the white squares. Bar=100 μm in the top panels and bar=200 μm in the bottom panels.
FIG. 1D shows DAB staining of tumor tissues from Control-peptide-biotin treated mice counterstained with either hematoxylin (left) or eosin (right). The bottom images are larger versions of the areas within the white squares. Bar=100 μm in the top panels and bar=200 μm in the bottom panels.

FIG. 1A shows the peptide-SEAP constructs with insertion of the peptide-coding sequence directly before the stop codon (arrow). CMV shows the location of the Cytolmegalovirus promoter; IVS shows the location of the intron; SEAP shows the location of the SEAP-coding sequence; STOP shows the location of the Stop codon; and, pA shows the location of the bovine growth hormone polyadenylation signal. FIG. 1B shows T/S SEAP levels 72 hours after intramuscular electroporation of peptide-SEAP plasmid DNA in syngeneic CT26 (n=3), SCCVII (n=4), AT84 (n=4), and 4T1 (n=4) tumor-bearing mice as well as xenogeneic MCF7 tumor-bearing mice (n=4). Columns represent the ratio of the control-normalized SEAP/protein (pg/mg) in tumor to SEAP (pg/mL) in the serum and error bars represent SEM (* represent p<0.05 compared to wtSEAP). FIG. 1C shows DAB staining of tumor tissues from CHP-biotin treated mice counterstained with either hematoxylin (left) or eosin (right). The bottom images are larger versions of the areas within the white squares. Scale bars represent 100 μm in the top panels and 200 μm in the bottom panels. FIG. 1D shows DAB staining of tumor tissues from Control-peptide-biotin treated mice counterstained with either hematoxylin (left) or eosin (right). The bottom images are larger versions of the areas within the white squares. Scale bars represent 100 μm in the top panels and 200 μm in the bottom panels.

CHP, a linear peptide, repeatedly increased the T/S SEAP levels in several tumor models compared to wtSEAP. In Balb/c mice bearing colon carcinomas (CT26), CHP showed the greatest increase in T/S SEAP (FIG. 1B). To identify the peptides with potential for targeting multiple tumor models, some of these peptides were also tested in other models. In two squamous cell carcinoma models (SCCVII and AT84) in C3H mice, 5- and 7-fold increases in T/S SEAP were seen, respectively, for CHP-SEAP (FIG. 1B). In a breast adenocarcinoma model (4T1) in Balb/c mice, T/S SEAP was increased 15-fold for CHP-SEAP compared to wtSEAP (FIG. 1B). Importantly, the gene product targeting property of CHP was also confirmed in a xenogeneic human breast cancer model (MCF7) with a 4-fold increase in T/S SEAP (FIG. 1B), which suggests this peptide has potential application for human tumors. Thus the CHP peptide may be used as a tumor-targeting enhancer when fused with another protein.

Figure 8:
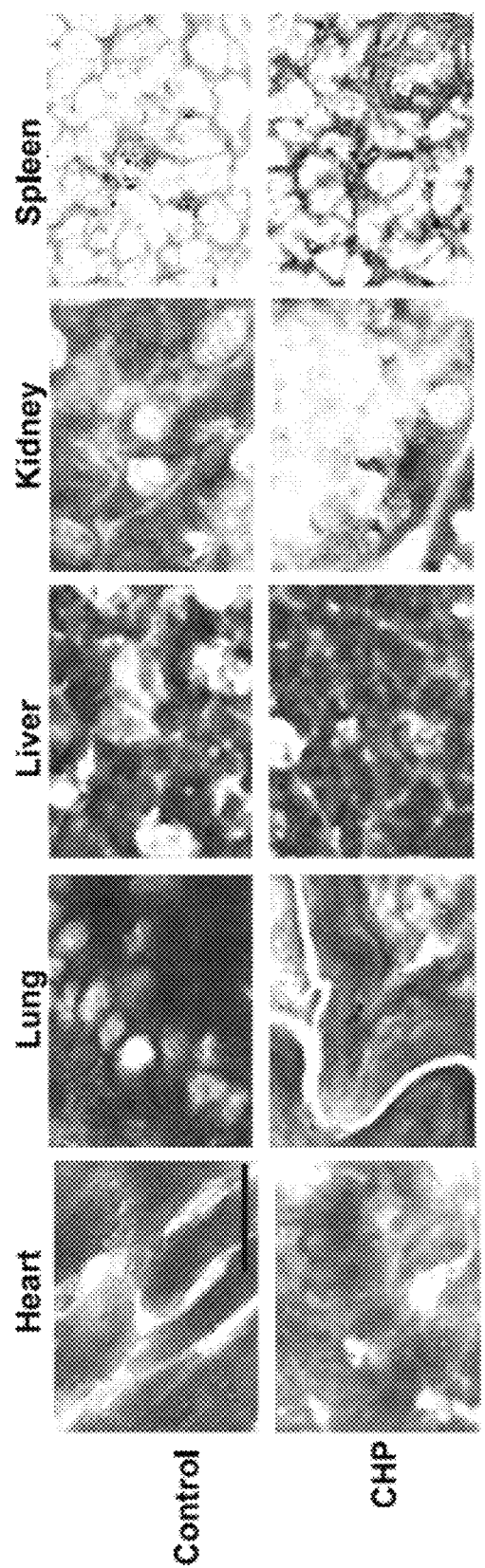
FIG. 8 shows sections from the hearts, lungs, livers, kidneys, and spleens from the same mice in FIG. 2B, FIG. 2C and FIG. 2D, counterstained with eosin only.

In addition to the quantitative T/S SEAP data above, we were interested in visualizing the CHP distribution in the tumors and throughout the body. To easily detect the localization of this targeted peptide, synthetic CHP-biotin conjugate or a control-peptide-biotin conjugate (Control-biotin) were injected into the tail vein of SCCVII tumor bearing C3H mice. CHP preferentially accumulated deep into the tumor environment, and, as seen in slides counterstained with either hematoxylin (FIG. 1C, top and bottom left) or eosin (FIG. 1C, top and bottom right), the CHP-biotin localized in the tumor tissue (19.6±1.3 positive per field, n=5 fields). In contrast, Control-biotin was unable to penetrate deep into the tumor tissues (1.8±0.37 positive per field, n=5 fields, p<0.0001 compared to CHP-biotin) (FIG. 1D). Negligible levels of biotin accumulated in the hearts, lungs, livers, and kidneys of mice treated with either CHP- or Control-biotin; however, similar levels of CHP-biotin and Control-biotin were detected in the spleens (FIG. 8), most likely due to non-specific uptake by the efficient mononuclear phagocytes bounding splenic red pulp sinuses.

Example 3

CHP-IL-12 Gene Product Maintains Targeting and Biological Functions

Peptide-IL-12 fusion gene constructs were generated by inserting the peptide coding sequences directly before the stop codon of the p40 subunit in an IL-12 plasmid DNA (FIG. 2A) [20]. CHP-IL-12, CDGRC-IL-12, wtIL-12, or empty vector plasmid DNA were transfected into 4T1 cells. After 24 hours, equivalent levels, approximately 175 pg/μL, of the IL-12p70 heterodimer were detected in the medium of all three IL-12 gene plasmid DNA transfected cells, and negligible IL-12p70 was detected in the control wells (FIG. 2B). Transferring the IL-12 containing medium to splenocytes induced similar levels of IFN-γ, a hallmark of IL-12 function (FIG. 2C) indicating that these fusion IL-12 proteins possess the same biological function as wtIL-12.

The distribution of CHP-IL-12 in the tumor, kidney, liver, and serum was determined via IL-12p70 ELISA 72 hours after treating CT26 tumor-bearing IL-12 knockout Balb/c ($IL-12^{-/-}$) mice with the CHP-IL-12 and wtIL-12 plasmid DNA. The CHP-IL-12 protein localized in the tumor environment as seen by the 4-fold increase in T/S IL-12 ratio compared to wtIL-12 (FIG. 2D). Likewise, CHP-IL-12 increased the Tumor/Kidney, Tumor/Liver, and Tumor/Spleen IL-12 ratios compared to wtIL-12 (FIG. 2D). So, a single copy of the CHP peptide is capable of targeting each IL-12 molecule to the tumor microenvironment.

Example 4

Figure 3D:
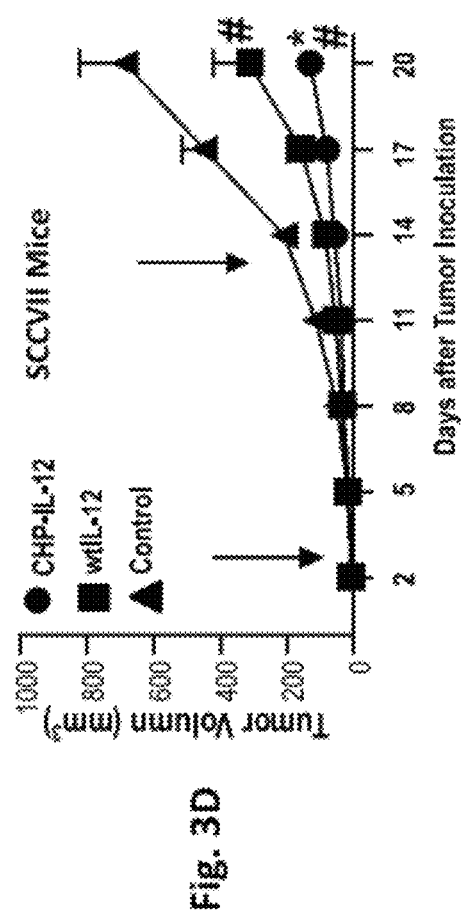
FIG. 3D shows tumor growth following treatments with CHP-IL-12, wtIL-12, and control plasmid DNA in SCCVII tumor-bearing C3H mice (n=5; * represents p<0.05 on days 17 and 20 compared to wtIL-12 plasmid DNA and control plasmid DNA).

CHP-IL-12 Fusion Gene Therapy Increases Inhibition of Primary and Metastatic Tumor Growth and Extends Survival Balb/c mice bearing 4T1 or CT26 tumors and C3H mice bearing SCCVII tumors were treated via i.m EP with empty (Control), wild type IL-12 (wtIL-12), and CHP-IL-12 (CHP-IL-12) fusion gene plasmid DNA. The treatments were repeated 10 days later. In the highly aggressive syngeneic 4T1 model, CHP-IL-12 gene therapy, compared to wtIL-12 gene therapy, significantly inhibited tumor growth ($p<0.05$ at day and $p<0.001$ from day 33 until day 42), while both wtIL-12 and CHP-IL-12 treated tumors were less voluminous than control DNA treated mice (FIG. 3A). Likewise, CHP-IL-12 treatments extend survival further than wtIL-12 and Control ($p<0.05$ compared to wtIL-12 plasmid DNA and $p<0.001$ compared to control plasmid DNA; FIG. 3C). In the same tumor model and treatment regimen, CHP-IL-12 gene therapy reduced by half the number of spontaneous metastatic nodules in the lungs compared to wtIL-12 ($p<0.05$ compared to wtIL-12 plasmid DNA; FIG. 3B). Similarly, in the SCCVII model CHP-IL-12 improves tumor growth inhibition compared to wtIL-12 ($p<0.05$ on days 17 and 20; FIG. 3D) and extends survival of mice compared to both Control and wtIL-12 ($p<0.05$; FIG. 3E).

Figure 3F:
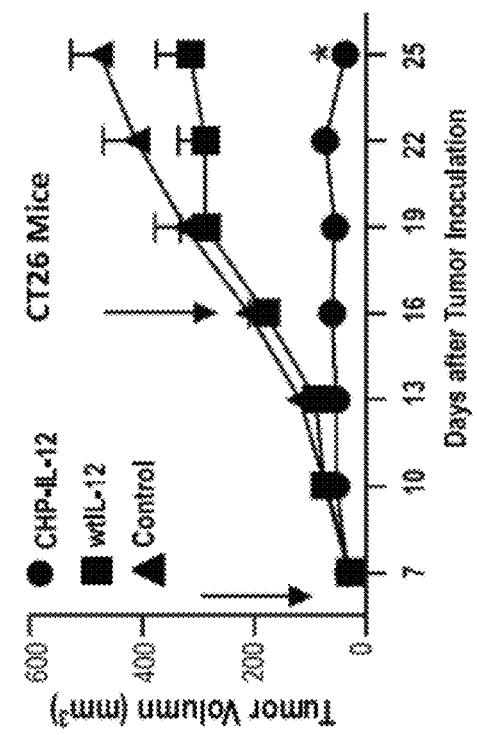
FIG. 3F shows tumor growth following treatments with CHP-IL-12, wtIL-12, and control plasmid DNA in CT26 tumor-bearing balb/c mice (n=5; * represents p<0.05 compared to wtIL-12 plasmid DNA, n=4, on day 25, and control plasmid DNA, n=3, on days 19 through 25). Black arrows represent treatments, and error bars represent SEM.
Figure 3E:
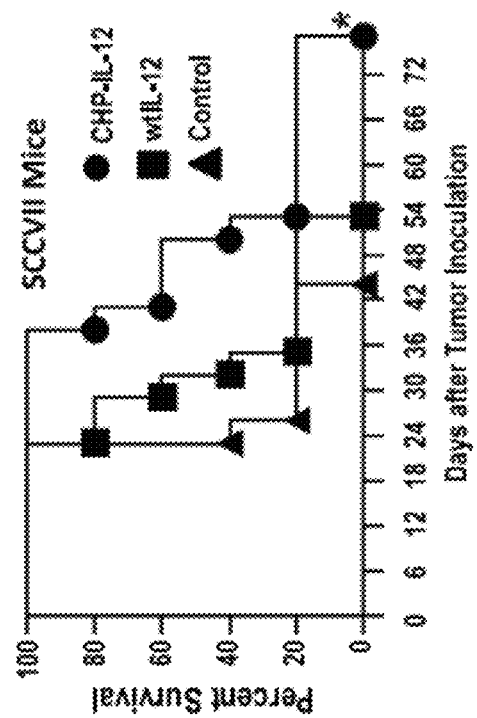
FIG. 3E shows Kaplan-Meier survival analysis of the SCCVII tumor-bearing C3H mice treated with CHP-IL-12, wtIL-12, and control plasmid DNA (* represents p<0.05 compared to wtIL-12 and control plasmid DNA).

In a third syngeneic model, CT26, CHP-IL-12 treatments inhibit tumor volumes starting only a few days after one treatment ($p<0.05$ compared to wtIL-12 plasmid DNA on day 25 and control plasmid DNA on days 19 through 25), and tumors begin to regress after the second treatment (FIG. 3F). After day 25, tumors in both wtIL-12 and CHP-IL-12 treated mice began to be eradicated. By day 55, 100% of mice treated with CHP-IL-12 were tumor-free while only 75% of wtIL-12 treated mice were tumor-free.

Figure 4A:
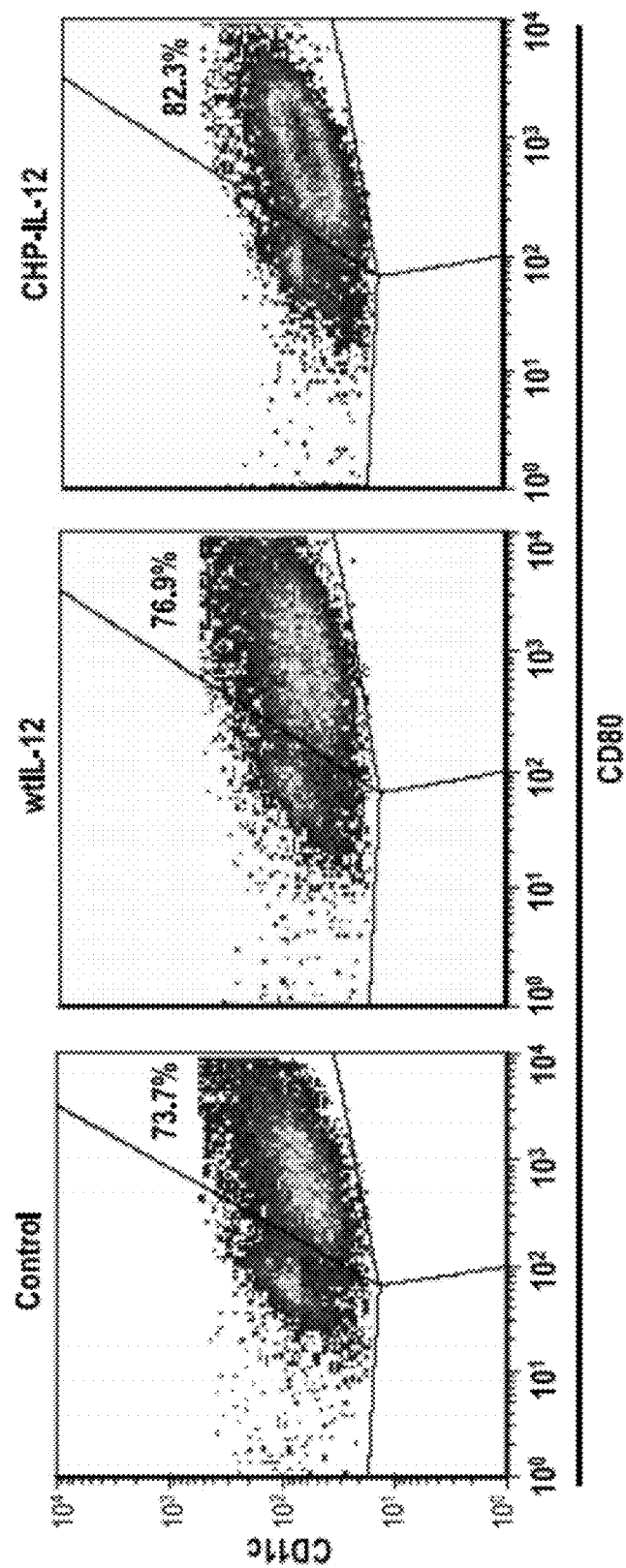
FIG. 4A shows fluorescence-activated cell sorting (FACS) analysis of tumor infiltrating cells isolated from SCCVII tumors from C3H mice following intravenous (i.v.) injection of Control, wtIL-12, or CHP-II-12, with or without depletion of vimentin with a co-injection of purified polyclonal goat anti-vimentin (100 μg) in the same i.v. injection as the peptide-biotin collected 7 days after the second treatment. The top right quadrant of the dot plot representation of cells gated for CD11c$^+$ represents activated DC (CD80$^{hi}$).
Figures 4B, 4C:
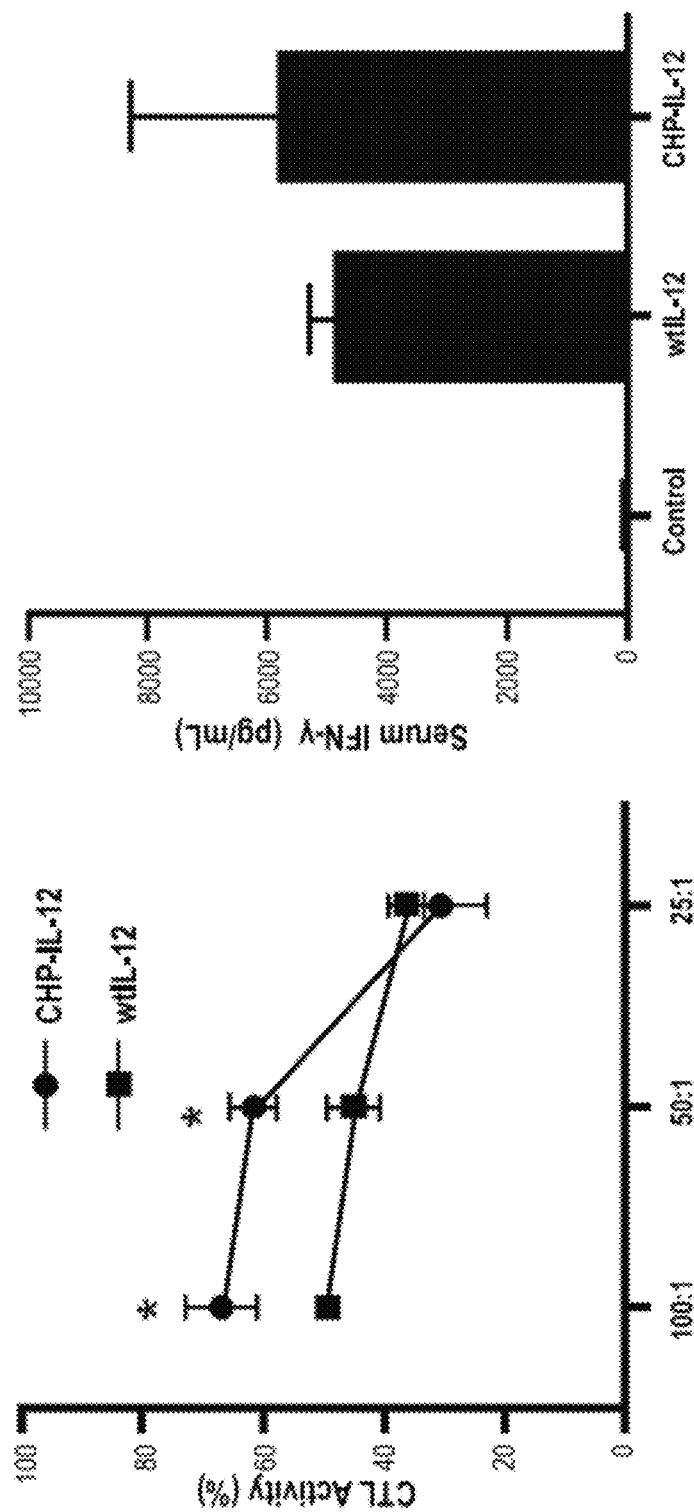
FIG. 4B shows tumor-specific cytotoxic T lymphocyte (CTL) activity from wtIL-12 and CHP-IL-12 fusion gene plasmid DNA treated mice bearing orthotopic EMT6 (a transplantable mouse mammary tumor cell line) tumors collected (* represents p<0.05).
FIG. 4C shows serum IFN-γ levels from 4T1-tumor bearing Balb/c 3 days after treatments with CHP-IL-12, wtIL-12, and control plasmid. Error bars represent SEM.

The CHP-IL-12 treatments increased the immune response to the tumor cells. To understand the mechanism by which CHP-IL-12 boosts inhibition of tumor growth as compared to wtIL-12, both CTL activity and tumor microenvironment immune cell profiling were analyzed. The rationale is that intratumoral injection, associated with a high level of IL-12 in tumors, boosted anti-tumor immune responses as compared to i.m. injection of IL-12 plasmid DNA, which is associated with a very low level of IL-12 in tumors [7]. Treatment with CHP-IL-12 increased the number of the tumor-infiltrating mature dendritic cells (DC) in the tumor environment as determined by FACS for $CD11c^{+/}$ $cD80^{hi}$ expression (FIG. 4A). Tumors from wtIL-12 treated mice contained 76.9% mature DC, an increase from 73.7% in control treated mice. This population in CHP-IL-12 treated mice was even higher at 82.3% (FIG. 4A). In agreement with this increase in mature DC in tumors, tumor-specific CTL activity was increased with CHP-IL-12 treated mice compared to wtIL-12 treated mice (FIG. 4B). Furthermore, CHP-IL-12 treatments did not cause any further increase in serum IFN-γ levels, so these immune responses are not the result of widespread IL-12 activity (FIG. 4C). These results suggest that CHP-IL-12 improves the anti-tumor immune response of effector cells in the tumor microenvironment.

Figure 9:
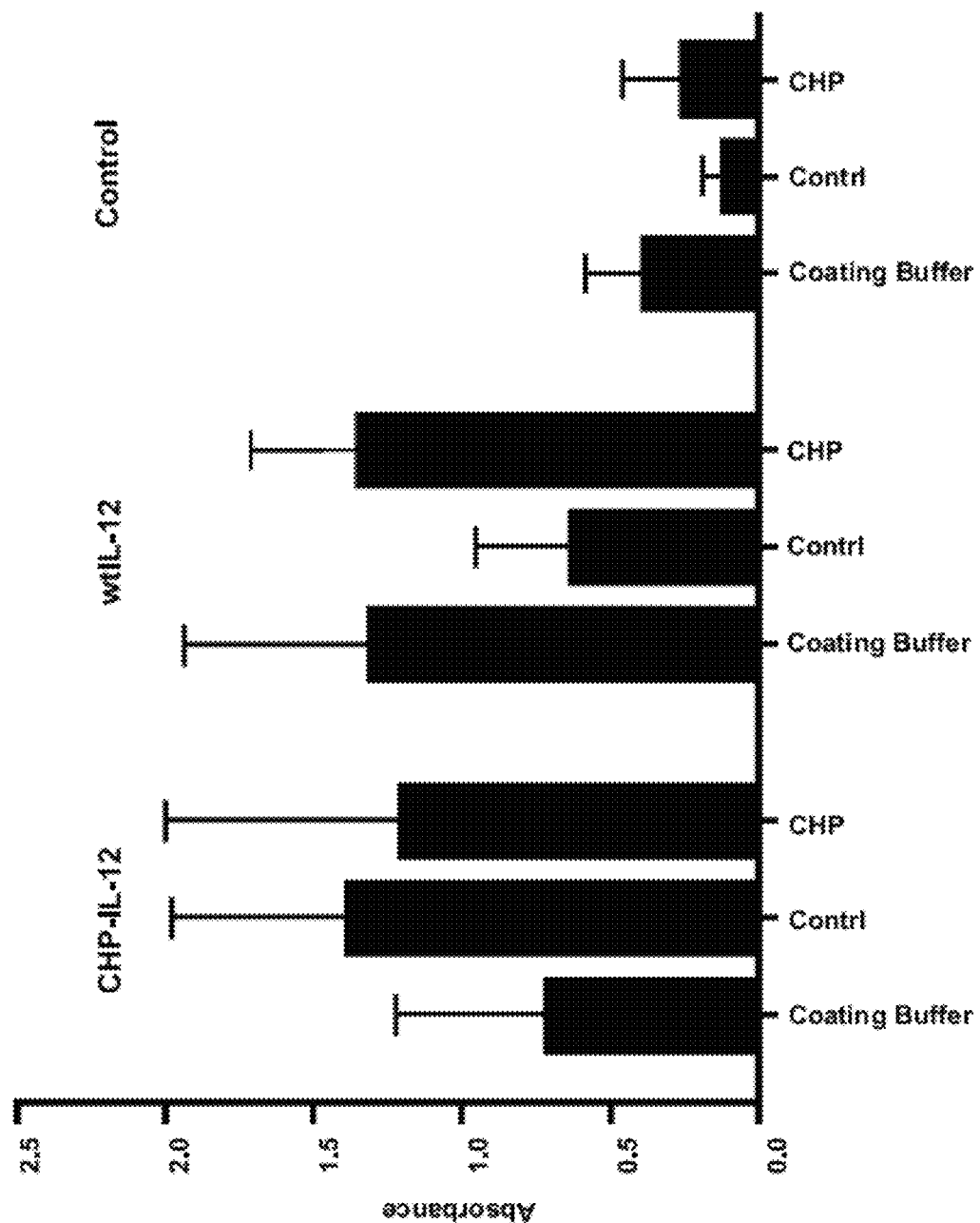
FIG. 9 shows the level of CHP-specific IgG from EMT6-tumor bearing Balb/c mice treated with wtIL-12 or CHP-IL-12 gene therapy as determined via binding to wells of a microwell plate coated with coating buffer only, control peptide or CHP peptide (n=3).

As with any treatment which includes the introduction of a foreign substance, CHP has the potential of eliciting the production of CHP-specific antibodies. To determine if these antibodies against the CHP-IL-12 gene product were being produced, a sandwich ELISA was developed using wells coated with buffer only, a control peptide, or CHP (capture "antibody") and biotin conjugated goat anti-mouse IgG (detection antibody) with avidin-HRP as the signal. There were no significant differences in the levels of IgG retained among serum samples from EMT6 tumor-bearing mice treated with control, wtIL-12 or CHP-IL-12 plasmid DNAs showing that CHP-IL-12 is not immunogenic (FIG. 9).

Example 5

CHP Homes to Vimentin Expressed in the Tumor Environment

Figure 5A:
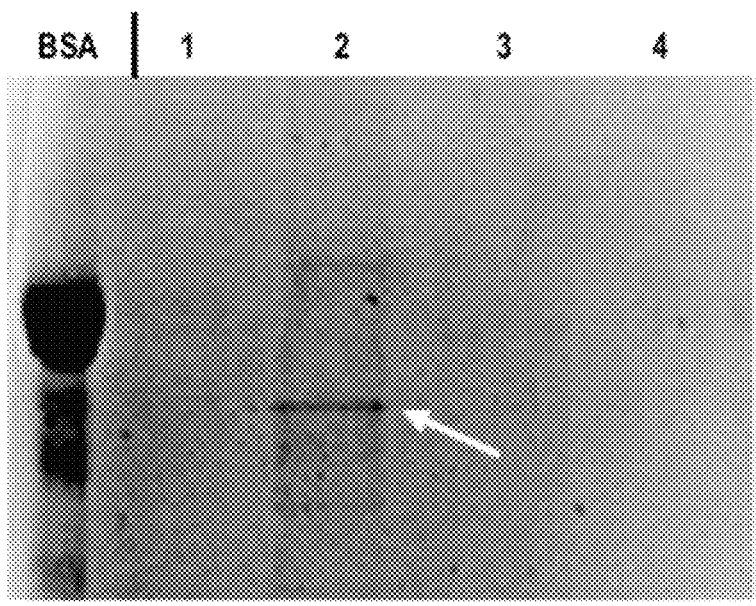
FIG. 5A shows SDS-PAGE (sodium dodecyl sulfate-polyacrylamide gel electrophoresis) analysis of potential receptors for CHP isolated via affinity chromatography of a pool of cell-surface proteins isolated from SCCVII cells. The only distinct band (arrow) was located in the second fraction, and mass spectrometry identified this band as vimentin. "BSA" represents bovine serum albumin.
Figure 5B:
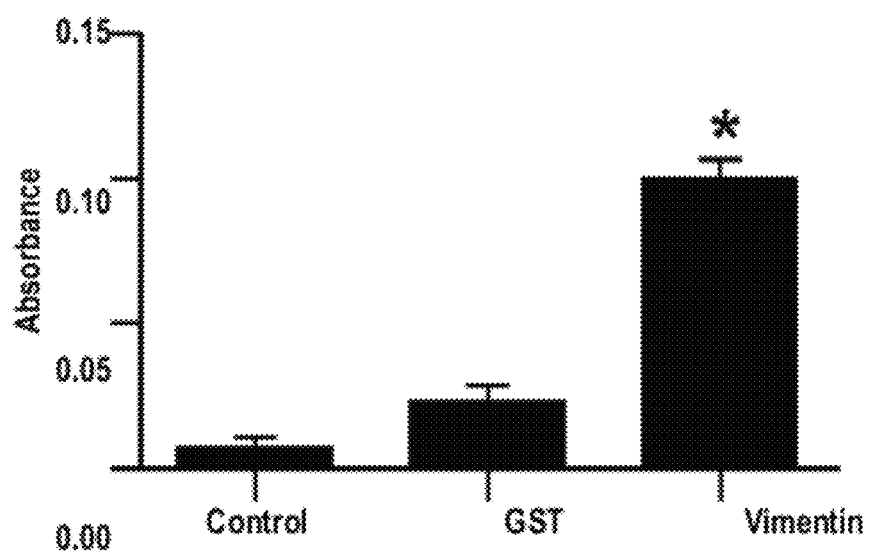
FIG. 5B shows the interaction of CHP-biotin with recombinant vimentin-GST (Vimentin), GST, and coating buffer only (control) coated wells of a polystyrene plate (n=6; * represents p<0.001 compared to both GST and Control, errors bars represent SEM).
Figure 10:
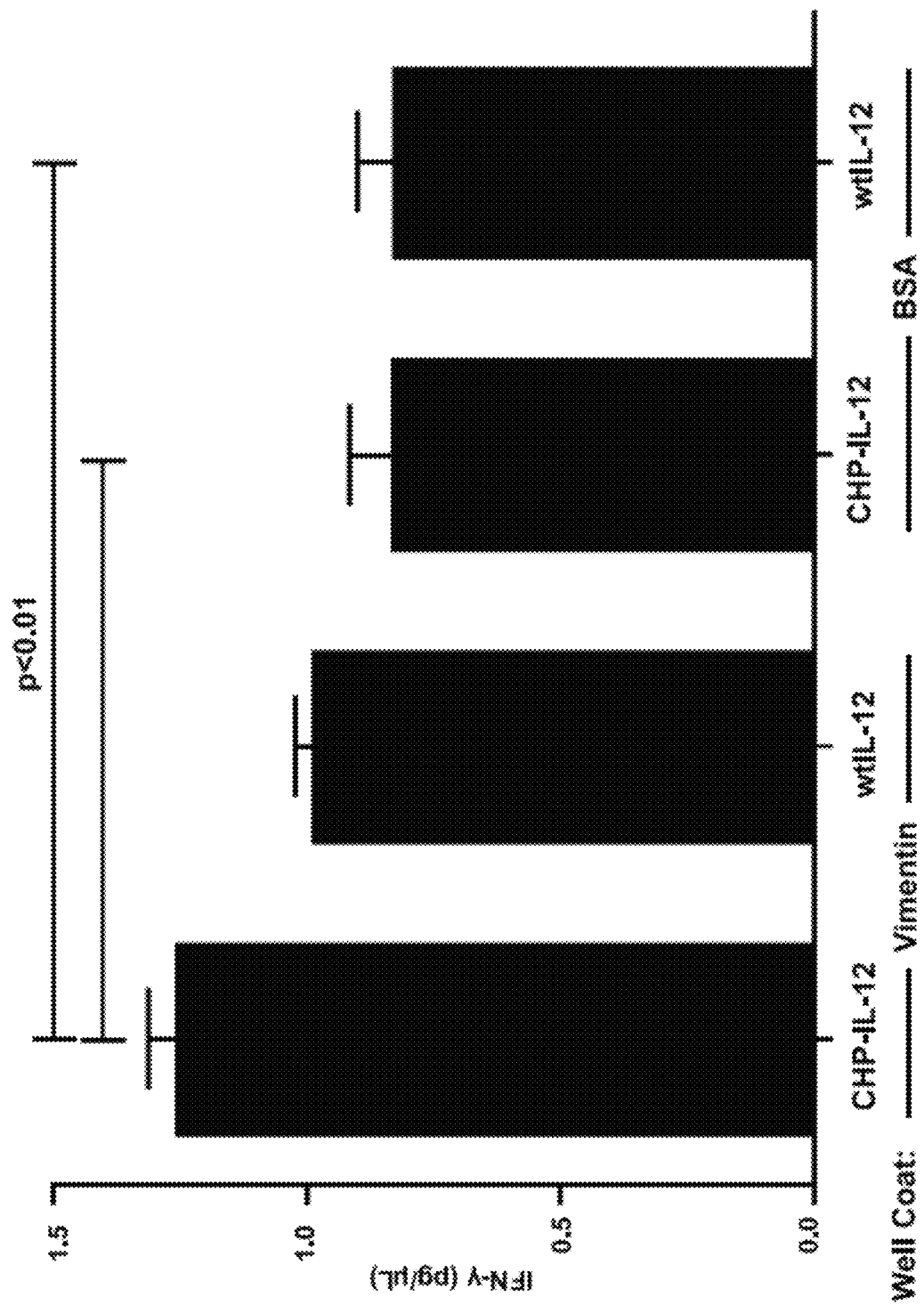
FIG. 10 shows the activity of CHP-SEAP when bound to vimentin. The induction of IFN-γ from splenocytes by CHP-IL12 and wtIL12 was compared when in the presence of vimentin or BSA. Error bars represent SEM and n=3.

CHP-biotin was used to isolate the CHP receptor from a pool of cell-surface receptor proteins isolated from SCCVII cells. Mass spectrometry of the isolated protein (FIG. 5A, arrow) identified this protein as vimentin. To validate this receptor, CHP-biotin was added to wells of a polystyrene plate that were coated with coating buffer only, GST, or recombinant Vimentin-GST. Indeed, CHP interacts with vimentin as the vimentin-coated wells retained a significantly higher level of HRP activity (FIG. 5B). To confirm that the interaction of CHP and vimentin did not inhibit the IL-12 activity, CHP-IL-12 and wtIL-12 were transferred to separate wells coated with either vimentin or BSA (1:1 molar ratio of IL-12 and vimentin), and then an hour later murine splenocytes were added to the wells. Interestingly, the CHP-IL-12 bound to vimentin coated wells induced a small but significantly higher level of IFN γ than both CHP-IL-12 and wtIL-12 in the BSA-coated wells (n=3, $p<0.05$, FIG. 10).

Figure 5C:
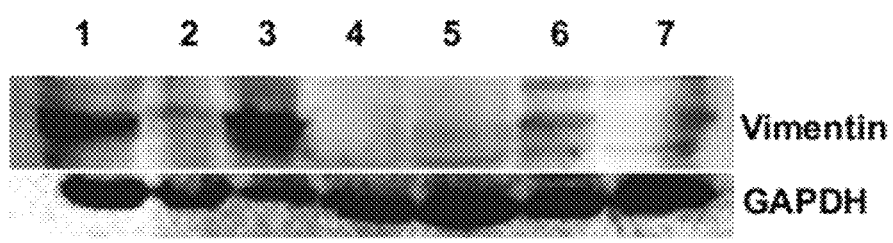
FIG. 5C shows Western blot analysis of vimentin expression in an SCCVII tumor (1) and heart (2), lung (3), liver (4), kidney (5), spleen (6), and serum (7) from SCCVII-tumor bearing C3H mice. "GAPDH" represents glyceraldehyde 3-phosphate dehydrogenase.
Figure 5D:
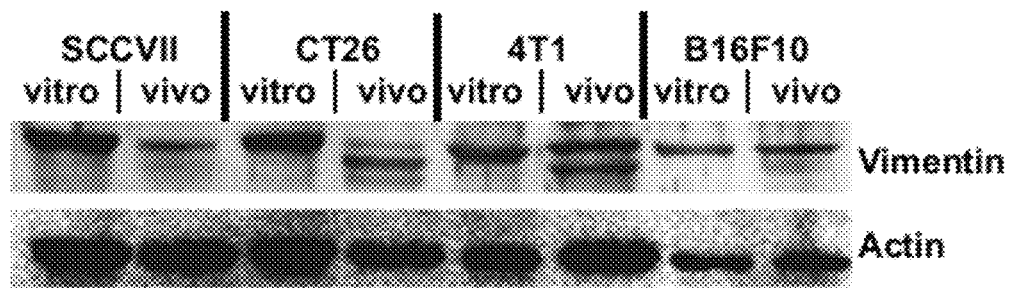
FIG. 5D shows Western blot analysis of vimentin expression in in vitro and ex vivo tumor samples from SCCVII, CT26, 4T-1, and B16F10 tumors.

To determine the levels of vimentin expression in normal tissues versus tumors, tissue lysates from an SCCVII tumor, heart, lung, liver, kidney, spleen, and serum from a C3H mouse were probed for vimentin expression via western blot analysis (WB). Very low levels of vimentin were detected in the heart, liver, kidney, spleen, and serum (FIG. 5C, lanes 2 and 4 through 7) while high levels of vimentin were detected in the tumor and lung (FIG. 5C, lanes 1 and 3). Similarly, analysis of vimentin expression in SCCVII, CT26, 4T1, and B16F10 (melanoma cell line derived from C57Bl/6 mice) tumor cell lines and ex vivo tumor tissues shows that all these tumor cell lines and their respective tumor models express vimentin (FIG. 5D), which explains universal tumor homing property as illustrated in FIG. 1.

Figure 5E:
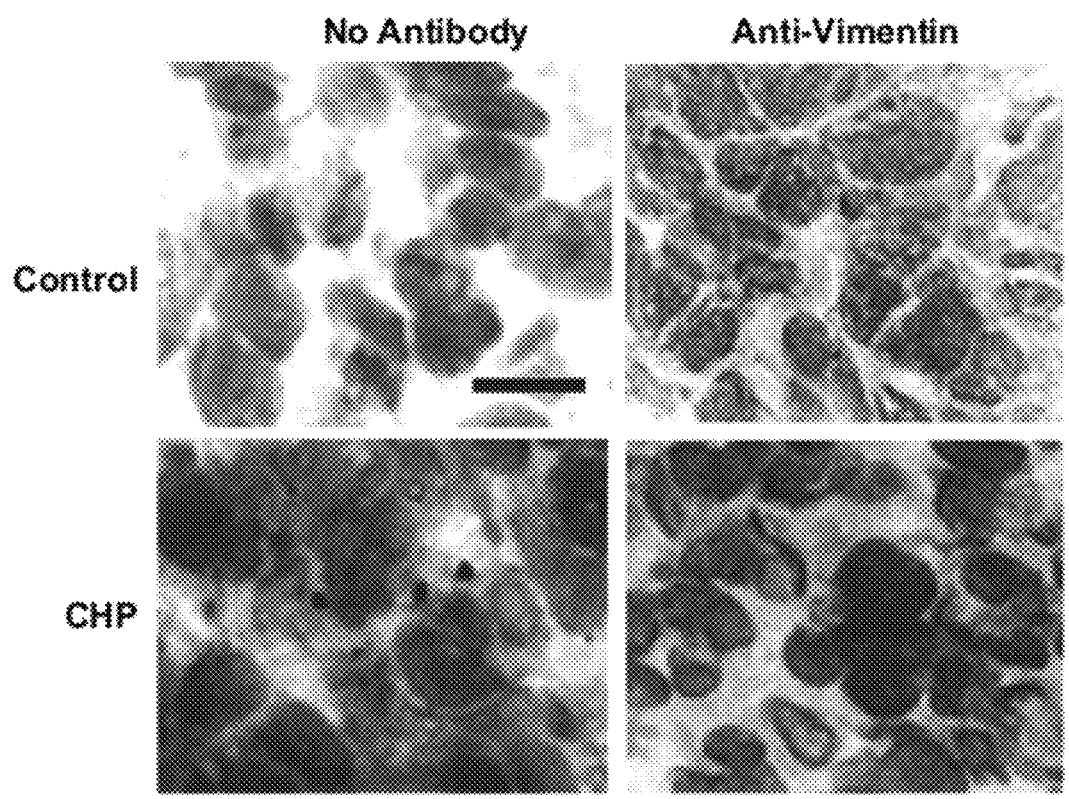
FIG. 5E shows accumulation of peptide-biotin in syngeneic SCCVII tumor bearing C3H mice following i.v. injection of either Control-biotin (top left and right) or CHP-biotin (bottom left and right), with (top and bottom right) or without (top and bottom left) depletion of vimentin with a co-injection of purified polyclonal goat anti-vimentin (100 µg) in the same i.v. injection as the peptide-biotin.

To determine that vimentin is the receptor protein interacting with CHP which is responsible for tumor homing, we performed tail vein injections of Control-biotin and CHP-biotin with or without blocking vimentin using purified polyclonal goat anti-vimentin in SCCVII tumor-bearing C3H mice. As expected, injection of Control-biotin with or without anti-vimentin did not result in any accumulation of peptide in the tumor (FIG. 5E, top left and top right, 1.8±0.37 with anti-vimentin and 2.6±0.51 without anti-vimentin, n=5). However, CHP-biotin did accrue in the tumor environment (FIG. 5E, bottom left, 19.6±1.3 positive per field, n=5, p<0.0001 compared to all other groups), but co-administration with anti-vimentin almost completely inhibited the tumor targeting ability of CHP (FIG. 5E, bottom right, 1.2±0.58 positive per field, n=5).

Example 6

CHP-IL-12 Reduces the Level of Toxic Lesions in the Liver

Figure 6A:
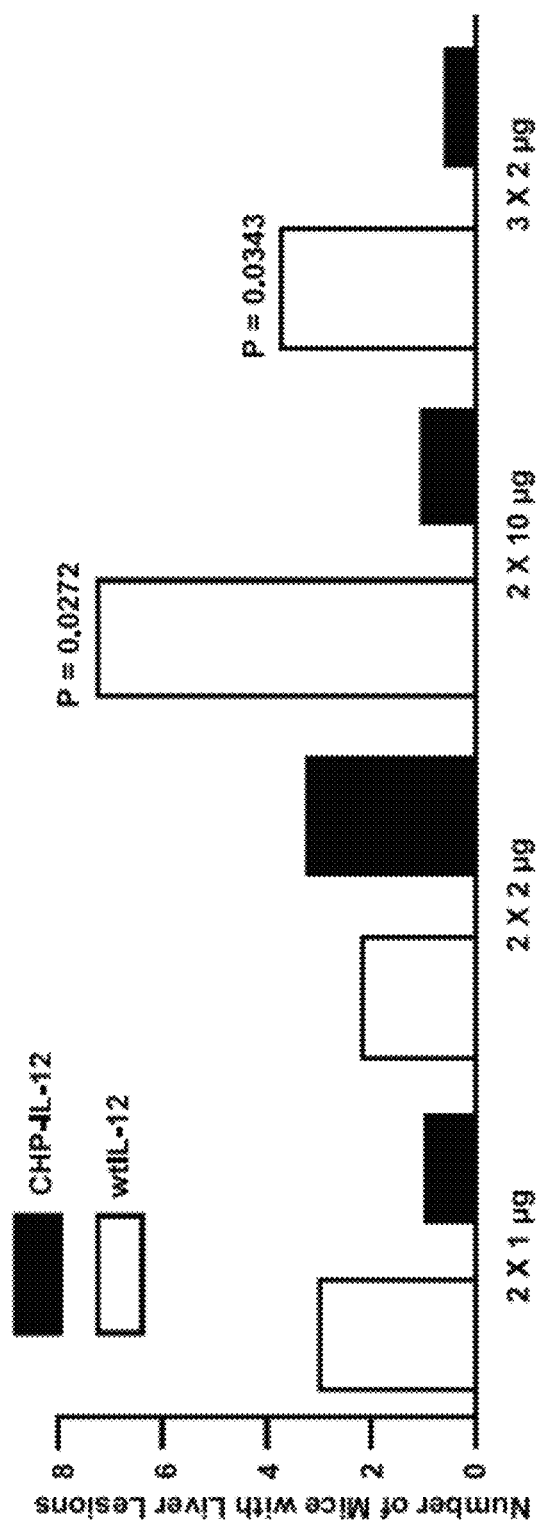
FIG. 6A shows the number of SCCVII tumor-bearing C3H mice with toxic lesions on the liver following two treatments of 1 µg (2×1 µg), 2 µg (2×2 µg), or 10 µg (2×10 µg) or three treatments of 2 µg (3×2 µg) of wtIL-12 or CHP-IL-12 (n=12).
Figure 6B:
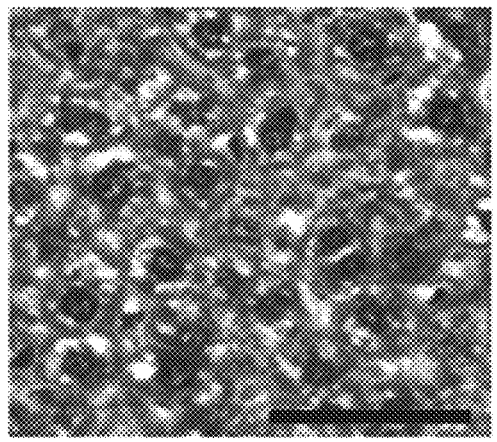
FIG. 6B shows a representative image of a normal liver area from the SCCVII tumor-bearing C3H mice. Scale bar represents 50 µm.
Figure 6C:
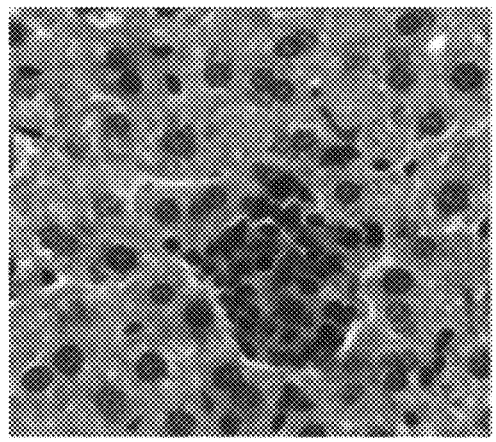
FIG. 6C shows a representative image of a toxic lesion from the SCCVII tumor-bearing C3H mice. Scale bar represents 50 µm.
Figure 6D:
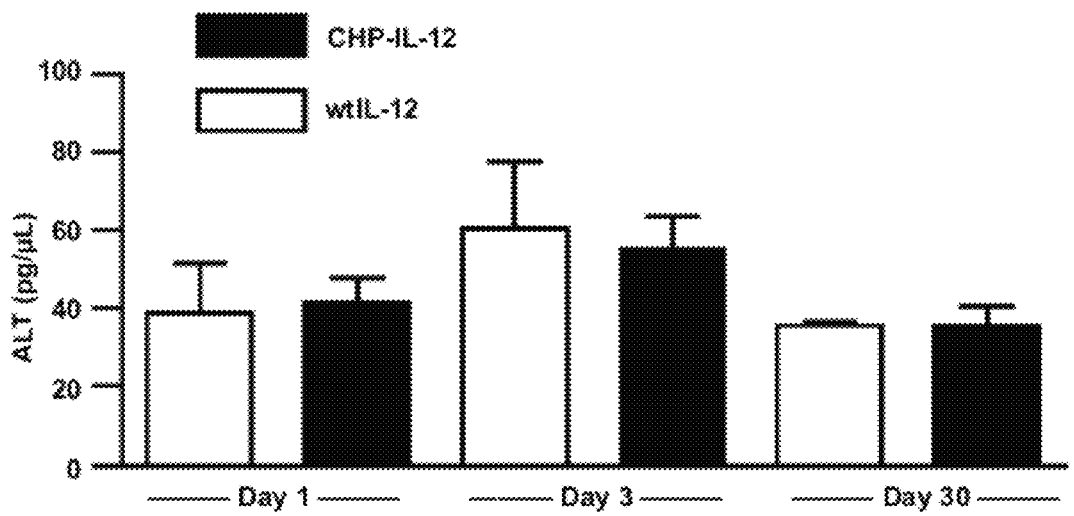
FIG. 6D shows levels of alanine transaminase (ALT), a key indicator of liver function, for both plasmid DNA treatments (wtIL-12 and CHP-IL-12) at all DNA levels and difference time points.

IL-12 induces liver toxicity (unpublished data). To test the hypothesis that the tumor-homing CHP-IL-12 reduced liver toxicity, SCCVII tumor-bearing C3H mice were treated with two treatments of 1 µg (2×1 µg), 2 µg (2×2 µg), or 10 µg (2×10 µg) or three treatments of 2 µg (3×2 µg) of wtIL-12 or CHP-IL-12, and mice were sacrificed on days 1, 3, and 30 after the final treatment. At low levels of plasmid DNA administration, 2×1 µg and 2×2 µg, there were no differences between wtIL-12 and CHP-IL-12 treatments; however, at the therapeutic level, 2×10 µg, and the triple treatment, 3×2 µg, CHP-IL-12 treatments caused toxic lesions in only one mouse while wtIL-12 treatments had significantly higher numbers (FIG. 6A). Serum chemistry profiles of these mice revealed that there were no differences between any treatment, regimen, or time points, and all levels for the hallmarks of toxicity, such as Alanine Transaminase, were within the normal range (FIG. 6D). So, CHP-IL-12 reduces the level of toxicity in the liver and does not cause any other detectable systemic toxicities.

In addition, other mini-peptide gene constructs were produced by inserting the peptide coding sequences into the p40 subunit-coding region of the IL12 plasmid, identical to the method in which CHP-IL12 was produced. These constructs were compared to CHP-IL-12 (SEQ ID NO:3) for the effectiveness in reducing tumor volume in SCCVII tumor-bearing C3H mice using methods as described in Example 1. The other peptides were DFKLFAVY (SEQ ID NO:30), CPCFLLGCC (SEQ ID NO:31), CGNKRTRGC (SEQ ID NO: 32), APRPG (SEQ ID NO:33), CNGRC (SEQ ID NO:9), and CDCRGDCFC (SEQ ID NO:12).

REFERENCES

1. Kobayashi M, Fitz L, Ryan M, Hewick R M, Clark S C, Chan S, et al. (1989). Identification and purification of natural killer cell stimulatory factor (NKSF), a cytokine with multiple biologic effects on human lymphocytes. *J Exp Med* 170: 827-845.
2. Del Vecchio M, Bajetta E, Canova S, Lotze M T, Wesa A, Parmiani G, et al. (2007). Interleukin-12: biological properties and clinical application. *Clin Cancer Res* 13: 4677-4685.
3. Halin C, Rondini S, Nilsson F, Berndt A, Kosmehl H, Zardi L, et al. (2002). Enhancement of the antitumor activity of interleukin-12 by targeted delivery to neovasculature. *Nat Biotechnol* 20: 264-269.
4. Dela Cruz J S, Trinh K R, Morrison S L, Penichet M L (2000). Recombinant anti-human HER2/neu IgG3-(GM-CSF) fusion protein retains antigen specificity and cytokine function and demonstrates antitumor activity. *J Immunol* 165: 5112-5121.
5. Dickerson E B, Akhtar N, Steinberg H, Wang Z-Y, Lindstrom M J, Padilla M L, et al. (2004). Enhancement of the Antiangiogenic Activity of Interleukin-12 by Peptide Targeted Delivery of the Cytokine to {alpha}v{beta}3 Integrin. *Mol Cancer Res* 2: 663-673.
6. Colombo G, Curnis F, De Mori G M, Gasparri A, Longoni C, Sacchi A, et al. (2002). Structure-activity relationships of linear and cyclic peptides containing the NGR tumor-homing motif. *J Biol Chem* 277: 47891-47897.
7. Li S, Zhang L, Torrero M, Cannon M, Barret R (2005). Administration route- and immune cell activation-dependent tumor eradication by IL-12 electrotransfer. *Mol Ther* 12: 942-949.
8. Yamazaki M, Zhang R, Straus F H, Messina M, Robinson B G, Hashizume K, et al. (2002). Effective gene therapy for medullary thyroid carcinoma using recombinant adenovirus inducing tumor-specific expression of interleukin-12. *Gene Ther* 9: 64-74.
9. Okada Y, Okada N, Mizuguchi H, Takahashi K, Hayakawa T, Mayumi T, et al. (2004). Optimization of antitumor efficacy and safety of in vivo cytokine gene therapy using RGD fiber-mutant adenovirus vector for preexisting murine melanoma. *Biochim Biophys Acta* 1670: 172-180.
10. Gao J Q, Eto Y, Yoshioka Y, Sekiguchi F, Kurachi S, Morishige T, et al. (2007). Effective tumor targeted gene transfer using PEGylated adenovirus vector via systemic administration. *J Control Release* 122: 102-110.
11. Wang H, Chen K, Cai W, Li Z, He L, Kashefi A, et al. (2008). Integrin-targeted imaging and therapy with RGD4C-TNF fusion protein. *Mol Cancer Ther* 7: 1044-1053.
12. Maeda H, Fang J, Inutsuka T, Kitamoto Y (2003). Vascular permeability enhancement in solid tumor: various factors, mechanisms involved and its implications. *Int Immunopharmacol* 3: 319-328.
13. Craig R, Cutrera J, Zhu S, Xia X, Lee Y H, Li S (2008). Administering plasmid DNA encoding tumor vessel-anchored IFN-alpha for localizing gene product within or into tumors. *Mol Ther* 16: 901-906.
14. Work L M, Buning H, Hunt E, Nicklin S A, Denby L, Britton N, et al. (2006). Vascular Bed-Targeted in Vivo Gene Delivery Using Tropism-Modified Adeno-associated Viruses. *Molecular Therapy* 13: 638-693.
15. Dandachi N, Hauser-Kronberger C, More E, Wiesener B, Hacker G W, Dietze O, et al. (2001). Co-expression of tenascin-C and vimentin in human breast cancer cells indicates phenotypic transdifferentiation during tumour progression: correlation with histopathological parameters, hormone receptors, and oncoproteins. *J Pathol* 193: 181-189.
16. Matos J M, Witzmann F A, Cummings O W, Schmidt C M (2009). A pilot study of proteomic profiles of human hepatocellular carcinoma in the United States. *J Surg Res* 155: 237-243.
17. Moisan E, Girard D (2006). Cell surface expression of intermediate filament proteins vimentin and lamin B1 in human neutrophil spontaneous apoptosis. *J Leukoc Biol* 79: 489-498.

18. Ngan C Y, Yamamoto H, Seshimo I, Tsujino T, Man-i M, Ikeda J I, et al. (2007). Quantitative evaluation of vimentin expression in tumour stroma of colorectal cancer. *Br J Cancer* 96: 986-992.
19. Wang Z, Li Y, Kong D, Banerjee S, Ahmad A, Azmi A S, et al. (2009). Acquisition of epithelial-mesenchymal transition phenotype of gemcitabine-resistant pancreatic cancer cells is linked with activation of the notch signaling pathway. *Cancer Res* 69: 2400-2407.
20. Cutrera J, Dibra D, Xia X, Li S (2010). Enhancement of reporter gene detection sensitivity by insertion of specific mini-peptide-coding sequences. *Cancer Gene Ther* 17: 131-140.
21. Stoff-Khalili M A, Rivera A A, Nedeljkovic-Kurepa A, DeBenedetti A, Li X L, Odaka Y, et al. (2008). Cancer-specific targeting of a conditionally replicative adenovirus using mRNA translational control. *Breast Cancer Res Treat* 108: 43-55.
22. Corti A, Curnis F, Arap W, Pasqualini R (2008). The neovasculature homing motif NGR: more than meets the eye. *Blood* 112: 2628-2635.
23. Temming K, Schiffelers R M, Molema G, Kok R J (2005). RGD-based strategies for selective delivery of therapeutics and imaging agents to the tumour vasculature. *Drug Resist Updat* 8: 381-402.
24. Garanger E, Boturyn D, Jin Z, Dumy P, Favrot M C, Coil J L (2005). New multifunctional molecular conjugate vector for targeting, imaging, and therapy of tumors. *Mol Ther* 12: 1168-1175.
25. Huet D, Bagot M, Loyaux D, Capdevielle J, Conraux L, Ferrara P, et al. (2006). SC5 mAb represents a unique tool for the detection of extracellular vimentin as a specific marker of Sezary cells. *J Immunol* 176: 652-659.
26. Bhattacharya R, Gonzalez A M, Debiase P J, Trejo H E, Goldman R D, Flitney F W, et al. (2009). Recruitment of vimentin to the cell surface by beta3 integrin and plectin mediates adhesion strength. *J Cell Sci* 122: 1390-1400.
27. Creighton C J, Li X, Landis M, Dixon J M, Neumeister V M, Sjolund A, et al. (2009). Residual breast cancers after conventional therapy display mesenchymal as well as tumor-initiating features. *Proc Natl Acad Sci U S A* 106: 13820-13825.
28. Thiery J P (2002). Epithelial-mesenchymal transitions in tumour progression. *Nat Rev Cancer* 2: 442-454.
29. Gilles C, Polette M, Zahm J M, Tournier J M, Volders L, Foidart J M, et al. (1999). Vimentin contributes to human mammary epithelial cell migration. *J Cell Sci* 112 (Pt 24): 4615-4625.
30. Nieminen M, Henttinen T, Merinen M, Marttila-Ichihara F, Eriksson J E, Jalkanen S (2006). Vimentin function in lymphocyte adhesion and transcellular migration. *Nat Cell Biol* 8: 156-162.
31. Sancey L, Garanger E, Foillard S, Schoehn G, Hurbin A, Albiges-Rizo C, et al. (2009). Clustering and internalization of integrin alphavbeta3 with a tetrameric RGD-synthetic peptide. *Mol Ther* 17: 837-843.
32. Gafner V, Trachsel E, Neri D (2006). An engineered antibody-interleukin-12 fusion protein with enhanced tumor vascular targeting properties. *Int J Cancer* 119: 2205-2212.
33. Gafner S, Dietz B M, McPhail K L, Scott I M, Glinski J A, Russell F E, et al. (2006). Alkaloids from Eschscholzia californica and their capacity to inhibit binding of [3H]8-Hydroxy-2-(di-N-propylamino)tetralin to 5-HT1A receptors in Vitro. *J Nat Prod* 69: 432-435.
34. Zhu S, Lee D A, Li S (2010). IL-12 and IL-27 sequential gene therapy via intramuscular electroporation delivery for eliminating distal aggressive tumors. *J Immunol* 184: 2348-2354.

The complete disclosures of all references cited in this specification are hereby incorporated by reference. Also incorporated by reference is the complete disclosure of U.S. priority application Ser. No. 61/441,914, and J. Cutrera et al., "Discovery of a linear peptide for improving tumor targeting of gene products and treatment of distal tumors by IL-12 gene therapy," Molecular Therapy, Vo. 19, no. 8, pp. 1468-1477, August 2011 (published online Mar. 8, 2011). In the event of an otherwise irreconcilable conflict, however, the present specification shall control.

What is claimed:

1. A tumor-targeting conjugate comprising an anti-tumor therapeutic agent conjugated to a carcinoma homing peptide (CHP) wherein the CHP is SEO ID NO:1,
wherein the anti-tumor therapeutic agent is interleukin 12,
wherein the carcinoma homing peptide is directly coupled to the p40 subunit of interleukin 12, and
wherein the amino acid sequence of the conjugate is SEQ ID NO:3.

2. The conjugate as in claim 1, wherein the conjugate selectively binds vimentin on the surface of a tumor cell.

3. A viral or non-viral vector comprising a composition encoding the conjugate of claim 1.

4. The vector as in claim 3, wherein the composition is the DNA sequence of SEQ ID NO:4.

5. A plasmid construct comprising a composition encoding the conjugate of claim 1.

6. The plasmid as in claim 5, wherein the composition is the DNA sequence of SEQ ID NO:4.

7. A method to decrease the size of a mammalian tumor, said method comprising administering to the mammal the conjugate of claim 1 wherein the mammalian tumor is selected from one or more tumors of the group consisting of breast adenocarcinoma, squamous cell carcinoma, and colon carcinoma.

8. A method to inhibit growth of a mammalian tumor, said method comprising administering to the mammal the conjugate of claim 1 wherein the mammalian tumor is selected from one or more tumors of the group consisting of breast adenocarcinoma, squamous cell carcinoma, and colon carcinoma.

9. A method to inhibit growth of a mammalian tumor, said method comprising administering to the mammal the vector of claim 3 wherein the mammalian tumor is selected from one or more tumors of the group consisting of breast adenocarcinoma, squamous cell carcinoma, and colon carcinoma.

10. The method of or claim 9, wherein the composition is the DNA sequence of SEQ ID NO:4.

11. A method to inhibit growth of a mammalian tumor, said method comprising administering to the mammal the plasmid of claim 5 wherein the mammalian tumor is selected from one or more tumors of the group consisting of breast adenocarcinoma, squamous cell carcinoma, and colon carcinoma.

12. The method of claim 11, wherein the composition is the DNA sequence of SEQ ID NO:4.

* * * * *

SEQUENCE LISTING

```
<160> NUMBER OF SEQ ID NOS: 33

<210> SEQ ID NO 1
<211> LENGTH: 7
<212> TYPE: PRT
<213> ORGANISM: Artificial sequence
<220> FEATURE:
<223> OTHER INFORMATION: Synthesized

<400> SEQUENCE: 1

Val Asn Thr Ala Asn Ser Thr
1               5

<210> SEQ ID NO 2
<211> LENGTH: 21
<212> TYPE: DNA
<213> ORGANISM: Artificial sequence
<220> FEATURE:
<223> OTHER INFORMATION: Synthesized

<400> SEQUENCE: 2
gtcaacacgg ctaactcgac a                                                 21

<210> SEQ ID NO 3
```

<211> LENGTH: 344
<212> TYPE: PRT
<213> ORGANISM: Artificial sequence
<220> FEATURE:
<223> OTHER INFORMATION: Synthesized

<400> SEQUENCE: 3

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Val
                325                 330                 335

Asn Thr Ala Asn Ser Thr Lys Leu
            340
```

<210> SEQ ID NO 4
<211> LENGTH: 1035
<212> TYPE: PRT
<213> ORGANISM: Artificial sequence
<220> FEATURE:
<223> OTHER INFORMATION: Synthesized

<400> SEQUENCE: 4

```
Ala Thr Gly Thr Gly Thr Cys Cys Thr Cys Ala Gly Ala Ala Gly Cys
1               5                   10                  15

Thr Ala Ala Cys Cys Ala Thr Cys Thr Cys Cys Thr Gly Gly Thr Thr
            20                  25                  30

Thr Gly Cys Cys Ala Thr Cys Gly Thr Thr Thr Thr Gly Cys Thr Gly
        35                  40                  45

Gly Thr Gly Thr Cys Thr Cys Cys Ala Cys Thr Cys Ala Thr Gly Gly
    50                  55                  60

Cys Cys Ala Thr Gly Thr Gly Gly Gly Ala Gly Cys Thr Gly Gly Ala
65                  70                  75                  80

Gly Ala Ala Ala Gly Ala Cys Gly Thr Thr Thr Ala Thr Gly Thr Thr
                85                  90                  95

Gly Thr Ala Gly Ala Gly Gly Thr Gly Gly Ala Cys Thr Gly Gly Ala
            100                 105                 110

Cys Thr Cys Cys Cys Gly Ala Thr Gly Cys Cys Cys Cys Thr Gly Gly
        115                 120                 125

Ala Gly Ala Ala Ala Cys Ala Gly Thr Gly Ala Ala Cys Cys Thr Cys
    130                 135                 140

Ala Cys Cys Thr Gly Thr Gly Ala Cys Ala Cys Gly Cys Cys Thr Gly
145                 150                 155                 160

Ala Ala Gly Ala Ala Gly Ala Thr Gly Ala Cys Ala Thr Cys Ala Cys
                165                 170                 175

Cys Thr Gly Gly Ala Cys Cys Thr Cys Ala Gly Ala Cys Cys Ala Gly
            180                 185                 190

Ala Gly Ala Cys Ala Thr Gly Gly Ala Gly Thr Cys Ala Thr Ala Gly
        195                 200                 205

Gly Cys Thr Cys Thr Gly Gly Ala Ala Ala Gly Ala Cys Cys Cys Thr
    210                 215                 220

Gly Ala Cys Cys Ala Thr Cys Ala Cys Thr Gly Thr Cys Ala Ala Ala
225                 230                 235                 240

Gly Ala Gly Thr Thr Thr Cys Thr Ala Gly Ala Thr Gly Cys Thr Gly
                245                 250                 255

Gly Cys Cys Ala Gly Thr Ala Cys Ala Cys Cys Thr Gly Cys Cys Ala
            260                 265                 270

Cys Ala Ala Ala Gly Gly Ala Gly Gly Cys Gly Ala Gly Ala Cys Thr
        275                 280                 285

Cys Thr Gly Ala Gly Cys Cys Ala Cys Thr Cys Ala Cys Ala Thr Cys
    290                 295                 300

Thr Gly Cys Thr Gly Cys Thr Cys Cys Ala Cys Ala Ala Gly Ala Ala
305                 310                 315                 320

Gly Gly Ala Ala Ala Ala Thr Gly Gly Ala Ala Thr Thr Thr Gly Gly
                325                 330                 335

Thr Cys Cys Ala Cys Thr Gly Ala Ala Ala Thr Thr Thr Thr Ala Ala
            340                 345                 350

Ala Ala Ala Ala Thr Thr Thr Cys Ala Ala Ala Ala Ala Cys Ala Ala
        355                 360                 365

Gly Ala Cys Thr Thr Thr Cys Cys Thr Gly Ala Ala Gly Thr Gly Thr
    370                 375                 380

Gly Ala Ala Gly Cys Ala Cys Cys Ala Ala Ala Thr Thr Ala Cys Thr
385                 390                 395                 400
```

```
Cys Cys Gly Gly Ala Cys Gly Gly Thr Thr Cys Ala Cys Gly Thr Gly
                405                 410                 415

Cys Thr Cys Ala Thr Gly Gly Cys Thr Gly Gly Thr Gly Cys Ala Ala
            420                 425                 430
Ala Gly Ala Ala Ala Cys Ala Thr Gly Gly Ala Cys Thr Thr Gly Ala
        435                 440                 445

Ala Gly Thr Thr Cys Ala Ala Cys Ala Thr Cys Ala Ala Gly Ala Gly
    450                 455                 460

Cys Ala Gly Thr Ala Gly Cys Ala Gly Thr Thr Cys Cys Cys Cys Thr
465                 470                 475                 480
Gly Ala Cys Thr Cys Thr Cys Gly Gly Gly Cys Ala Gly Thr Gly Ala
                485                 490                 495

Cys Ala Thr Gly Thr Gly Gly Ala Ala Thr Gly Gly Cys Gly Thr Cys
            500                 505                 510

Thr Cys Thr Gly Thr Cys Thr Gly Cys Ala Gly Ala Gly Ala Ala Gly
        515                 520                 525

Gly Thr Cys Ala Cys Ala Cys Thr Gly Gly Ala Cys Cys Ala Ala Ala
    530                 535                 540

Gly Gly Gly Ala Cys Thr Ala Thr Gly Ala Gly Ala Ala Gly Thr Ala
545                 550                 555                 560

Thr Thr Cys Ala Gly Thr Gly Thr Cys Cys Thr Gly Cys Cys Ala Gly
                565                 570                 575

Gly Ala Gly Gly Ala Thr Gly Thr Cys Ala Cys Cys Thr Gly Cys Cys
            580                 585                 590

Cys Ala Ala Cys Thr Gly Cys Cys Gly Ala Gly Gly Ala Gly Ala Cys
        595                 600                 605

Cys Cys Thr Gly Cys Cys Cys Ala Thr Thr Gly Ala Ala Cys Thr Gly
    610                 615                 620

Gly Cys Gly Thr Thr Gly Gly Ala Ala Gly Cys Ala Cys Gly Gly Cys
625                 630                 635                 640

Ala Gly Cys Ala Gly Ala Ala Thr Ala Ala Ala Thr Ala Thr Gly Ala
                645                 650                 655

Gly Ala Ala Cys Thr Ala Cys Ala Gly Cys Ala Cys Cys Ala Gly Cys
            660                 665                 670

Thr Thr Cys Thr Thr Cys Ala Thr Cys Ala Gly Gly Gly Ala Cys Ala
        675                 680                 685

Thr Cys Ala Thr Cys Ala Ala Ala Cys Cys Ala Gly Ala Cys Cys Cys
    690                 695                 700

Gly Cys Cys Cys Ala Ala Gly Ala Ala Cys Thr Thr Gly Cys Ala Gly
705                 710                 715                 720

Ala Thr Gly Ala Ala Gly Cys Cys Thr Thr Thr Gly Ala Ala Gly Ala
                725                 730                 735

Ala Cys Thr Cys Ala Cys Ala Gly Gly Thr Gly Gly Ala Gly Gly Thr
            740                 745                 750

Cys Ala Gly Cys Thr Gly Gly Gly Ala Gly Thr Ala Cys Cys Cys Thr
        755                 760                 765

Gly Ala Cys Thr Cys Cys Thr Gly Gly Ala Gly Cys Ala Cys Thr Cys
    770                 775                 780

Cys Cys Cys Ala Thr Thr Cys Cys Thr Ala Cys Thr Thr Cys Thr Cys
785                 790                 795                 800

Cys Cys Thr Cys Ala Ala Gly Thr Thr Cys Thr Thr Thr Gly Thr Thr
                805                 810                 815
```

```
Cys Gly Ala Ala Thr Cys Cys Ala Gly Gly Cys Ala Ala Gly Ala
                820                 825                 830

Ala Ala Gly Ala Ala Ala Gly Ala Thr Gly Ala Ala Gly Gly Ala
            835                 840                 845

Gly Ala Cys Ala Gly Ala Gly Gly Ala Gly Gly Gly Thr Gly Thr
        850                 855                 860

Ala Ala Cys Cys Ala Gly Ala Ala Gly Gly Thr Gly Cys Gly Thr
865                 870                 875                 880

Thr Cys Cys Thr Cys Gly Thr Ala Gly Ala Gly Ala Gly Ala Cys
                885                 890                 895

Ala Thr Cys Thr Ala Cys Cys Gly Ala Ala Gly Thr Cys Cys Ala Ala
                900                 905                 910

Thr Gly Cys Ala Ala Gly Gly Cys Gly Gly Gly Ala Ala Thr Gly
            915                 920                 925

Thr Cys Thr Gly Cys Gly Thr Gly Cys Ala Ala Gly Cys Thr Cys Ala
        930                 935                 940

Gly Gly Ala Thr Cys Gly Cys Thr Ala Thr Thr Ala Cys Ala Ala Thr
945                 950                 955                 960

Thr Cys Cys Thr Cys Gly Thr Gly Cys Ala Gly Cys Ala Ala Gly Thr
                965                 970                 975

Gly Gly Gly Cys Ala Thr Gly Thr Gly Thr Thr Cys Cys Thr Gly
            980                 985                 990

Cys Ala Gly Gly Gly Thr Cys Cys  Gly Ala Thr Cys Cys  Gly Thr Cys
                995                 1000                1005

Ala Ala  Cys Ala Cys Gly Gly  Cys Thr Ala Ala Cys  Thr Cys Gly
        1010                1015                    1020

Ala Cys  Ala Ala Ala Gly Cys  Thr Thr Thr Gly Ala
        1025                1030                1035

<210> SEQ ID NO 5
<211> LENGTH: 8
<212> TYPE: PRT
<213> ORGANISM: Artificial sequence
<220> FEATURE:
<223> OTHER INFORMATION: Synthesized

<400> SEQUENCE: 5

Cys Gly Phe Glu Leu Glu Thr Cys
1               5

<210> SEQ ID NO 6
<211> LENGTH: 16
<212> TYPE: PRT
<213> ORGANISM: Artificial sequence
<220> FEATURE:
<223> OTHER INFORMATION: Synthesized

<400> SEQUENCE: 6

Asn Gly Tyr Glu Ile Glu Trp Tyr Ser Trp Val Thr His Gly Met Tyr
1               5                   10                  15

<210> SEQ ID NO 7
<211> LENGTH: 10
<212> TYPE: PRT
<213> ORGANISM: Artificial sequence
<220> FEATURE:
<223> OTHER INFORMATION: Synthesized

<400> SEQUENCE: 7

Thr Ala Ala Ser Gly Val Arg Ser Met His
```

<210> SEQ ID NO 8
<211> LENGTH: 7
<212> TYPE: PRT
<213> ORGANISM: Artificial sequence
<220> FEATURE:
<223> OTHER INFORMATION: Synthesized

<400> SEQUENCE: 8

Ala Thr Trp Leu Pro Pro Ala
1               5

<210> SEQ ID NO 9
<211> LENGTH: 5
<212> TYPE: PRT
<213> ORGANISM: Artificial sequence
<220> FEATURE:
<223> OTHER INFORMATION: Synthesized

<400> SEQUENCE: 9

Cys Asn Gly Arg Cys
1               5

<210> SEQ ID NO 10
<211> LENGTH: 12
<212> TYPE: PRT
<213> ORGANISM: Artificial sequence
<220> FEATURE:
<223> OTHER INFORMATION: Synthesized

<400> SEQUENCE: 10

His Thr Met Tyr Tyr His His Tyr Gln His His Leu
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthesized

<400> SEQUENCE: 11

Asn Ser Ser Arg Gly Leu Gly
1               5

<210> SEQ ID NO 12
<211> LENGTH: 9
<212> TYPE: PRT
<213> ORGANISM: Artificial sequence
<220> FEATURE:
<223> OTHER INFORMATION: Synthesized

<400> SEQUENCE: 12

Cys Asp Cys Arg Gly Asp Cys Phe Cys
1               5

<210> SEQ ID NO 13
<211> LENGTH: 5
<212> TYPE: PRT
<213> ORGANISM: Artificial sequence
<220> FEATURE:
<223> OTHER INFORMATION: Synthesized

<400> SEQUENCE: 13

Cys Asp Gly Arg Cys
1               5

<210> SEQ ID NO 14
<211> LENGTH: 20
<212> TYPE: DNA
<213> ORGANISM: Artificial sequence
<220> FEATURE:
<223> OTHER INFORMATION: Synthetic primer

<400> SEQUENCE: 14
ccaggatcct aaaagggcag                                            20

<210> SEQ ID NO 15
<211> LENGTH: 25
<212> TYPE: DNA
<213> ORGANISM: Artificial sequence
<220> FEATURE:
<223> OTHER INFORMATION: Synthetic primer

<400> SEQUENCE: 15
gtcgaccccg cccaagaact tgcag                                      25

<210> SEQ ID NO 16
<211> LENGTH: 42
<212> TYPE: DNA
<213> ORGANISM: Artificial sequence
<220> FEATURE:
<223> OTHER INFORMATION: Synthetic primer

<400> SEQUENCE: 16
gttcgaatct gcgatggaag atgccagcgc aagaaagaaa ag                   42

<210> SEQ ID NO 17
<211> LENGTH: 54
<212> TYPE: DNA
<213> ORGANISM: Artificial sequence
<220> FEATURE:
<223> OTHER INFORMATION: Synthetic primer

<400> SEQUENCE: 17
ttatcactcg aggcaagtct ctagctcgaa tccacatgtc tgctcgaagc ggcc      54

<210> SEQ ID NO 18
<211> LENGTH: 74
<212> TYPE: DNA
<213> ORGANISM: Artificial sequence
<220> FEATURE:
<223> OTHER INFORMATION: Synthetic primer

<400> SEQUENCE: 18
ttatcagtac ataccgtgag taacccagga gtaccactcg atctcgtaac cgtttgtctg 60
ctcgaagcgg ccgg                                                  74

<210> SEQ ID NO 19
<211> LENGTH: 56
<212> TYPE: DNA
<213> ORGANISM: Artificial sequence
<220> FEATURE:
<223> OTHER INFORMATION: Synthetic primer

<400> SEQUENCE: 19
ttatcaatgc atactacgga caccactagc agcagttgtc tgctcgaagc ggccgg    56

<210> SEQ ID NO 20
<211> LENGTH: 47
<212> TYPE: DNA

<210> SEQ ID NO 20
<211> LENGTH: 47
<212> TYPE: DNA
<213> ORGANISM: Artificial sequence
<220> FEATURE:
<223> OTHER INFORMATION: Synthetic primer

<400> SEQUENCE: 20
ttatcaagct ggagggagcc acgtagctgt ctgctcgaag cggccgg        47

<210> SEQ ID NO 21
<211> LENGTH: 41
<212> TYPE: DNA
<213> ORGANISM: Artificial sequence
<220> FEATURE:
<223> OTHER INFORMATION: Synthetic primer

<400> SEQUENCE: 21
ttatcaacaa cgaccgttac atgtctgctc gaagcggccg g        41

<210> SEQ ID NO 22
<211> LENGTH: 62
<212> TYPE: DNA
<213> ORGANISM: Artificial sequence
<220> FEATURE:
<223> OTHER INFORMATION: Synthetic primer

<400> SEQUENCE: 22
ttatcaaagg tgatgctgat agtgatggta atacatagtg tgtgtctgct cgaagcggcc        60
gg        62

<210> SEQ ID NO 23
<211> LENGTH: 43
<212> TYPE: DNA
<213> ORGANISM: Artificial sequence
<220> FEATURE:
<223> OTHER INFORMATION: Synthetic primer

<400> SEQUENCE: 23
tcgtctagat tatcacagac ttccacccgg gtgcgcggcg tcg        43

<210> SEQ ID NO 24
<211> LENGTH: 45
<212> TYPE: DNA
<213> ORGANISM: Artificial sequence
<220> FEATURE:
<223> OTHER INFORMATION: Synthetic primer

<400> SEQUENCE: 24
ttatcaaccg agatccctac tgctgtttgt ctgctcgaag cggcc        45

<210> SEQ ID NO 25
<211> LENGTH: 33
<212> TYPE: DNA
<213> ORGANISM: Artificial sequence
<220> FEATURE:
<223> OTHER INFORMATION: Synthetic primer

<400> SEQUENCE: 25
ttatcagcag aaacaatcac cgcggcaatc aca        33

<210> SEQ ID NO 26
<211> LENGTH: 58
<212> TYPE: DNA
<213> ORGANISM: Artificial sequence
<220> FEATURE:
<223> OTHER INFORMATION: Synthetic primer

<400> SEQUENCE: 26

```
actagtttat caaagctttg tcgagttagc cgtgttgacg gatcggaccc tgcaggga        58
```

<210> SEQ ID NO 27
<211> LENGTH: 19
<212> TYPE: DNA
<213> ORGANISM: Artificial sequence
<220> FEATURE:
<223> OTHER INFORMATION: Synthetic primer

<400> SEQUENCE: 27

```
gaacaaaagc tggtaccgg                                                   19
```

<210> SEQ ID NO 28
<211> LENGTH: 9
<212> TYPE: PRT
<213> ORGANISM: Artificial sequence
<220> FEATURE:
<223> OTHER INFORMATION: Synthesized

<400> SEQUENCE: 28

Val Asn Thr Ala Asn Ser Thr Gly Gly
1               5

<210> SEQ ID NO 29
<211> LENGTH: 18
<212> TYPE: PRT
<213> ORGANISM: Artificial sequence
<220> FEATURE:
<223> OTHER INFORMATION: Synthesized

<400> SEQUENCE: 29

Cys Thr Ser Thr Ser Pro Leu Pro Pro Pro Ser His Ser Thr Ser Lys
1               5                   10                  15

Lys Gly

<210> SEQ ID NO 30
<211> LENGTH: 8
<212> TYPE: PRT
<213> ORGANISM: Artificial sequence
<220> FEATURE:
<223> OTHER INFORMATION: Synthesized

<400> SEQUENCE: 30

Asp Phe Lys Leu Phe Ala Val Tyr
1               5

<210> SEQ ID NO 31
<211> LENGTH: 9
<212> TYPE: PRT
<213> ORGANISM: Artificial sequence
<220> FEATURE:
<223> OTHER INFORMATION: Synthesized

<400> SEQUENCE: 31

Cys Pro Cys Phe Leu Leu Gly Cys Cys
1               5

<210> SEQ ID NO 32
<211> LENGTH: 9
<212> TYPE: PRT
<213> ORGANISM: Artificial sequence
<220> FEATURE:
<223> OTHER INFORMATION: Synthesized

<400> SEQUENCE: 32

```
Cys Gly Asn Lys Arg Thr Arg Gly Cys
1               5

<210> SEQ ID NO 33
<211> LENGTH: 5
<212> TYPE: PRT
<213> ORGANISM: Artificial sequence
<220> FEATURE:
<223> OTHER INFORMATION: Synthesized

<400> SEQUENCE: 33

Ala Pro Arg Pro Gly
1               5
```